United States Patent
Tsukagoshi et al.

(10) Patent No.: US 8,884,958 B2
(45) Date of Patent: Nov. 11, 2014

(54) IMAGE PROCESSING SYSTEM AND METHOD THEREOF

(75) Inventors: Shinsuke Tsukagoshi, Nasushiobara (JP); Go Mukumoto, Utsunomiya (JP); Masao Yui, Otawara (JP); Tatsuo Maeda, Nasushiobara (JP); Akira Adachi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 48 days.

(21) Appl. No.: 13/490,589

(22) Filed: Jun. 7, 2012

(65) Prior Publication Data

US 2012/0313943 A1 Dec. 13, 2012

(30) Foreign Application Priority Data

Jun. 9, 2011 (JP) ................. 2011-129368

(51) Int. Cl.
*G06T 17/00* (2006.01)
*G06T 15/00* (2011.01)
(Continued)

(52) U.S. Cl.
CPC ........ *H04N 13/0278* (2013.01); *G02B 27/2264* (2013.01); *A61B 6/501* (2013.01); *G06T 2210/41* (2013.01); *A61B 8/13* (2013.01); *A61B 6/468* (2013.01); *A61B 8/466* (2013.01); *A61B 8/523* (2013.01); *A61B 6/5235* (2013.01); *A61B 5/055* (2013.01); *G06T 19/00* (2013.01); *A61B 6/5223* (2013.01); *A61B 6/5217* (2013.01); *A61B 6/4417* (2013.01); *A61B 6/466* (2013.01); *A61B 6/037* (2013.01); *A61B 6/022* (2013.01); *A61B 6/484* (2013.01); *H04N 5/445* (2013.01)
USPC .......................................... 345/424; 345/419

(58) Field of Classification Search
CPC ..... G06T 15/08; G06T 2210/41; G06T 15/00; G06T 2207/10012; G06T 2207/10072; G06T 2207/10116; G06T 7/0012; G09G 3/003; G09G 5/14
USPC ........... 345/424, 419, 420; 382/128; 600/443, 600/426; 358/1.6; 348/51
See application file for complete search history.

(56) References Cited

U.S. PATENT DOCUMENTS

2003/0112503 A1   6/2003 Lantin
2005/0059886 A1*  3/2005 Webber .................. 600/426
(Continued)

FOREIGN PATENT DOCUMENTS

CN   101374244 A   2/2009
CN   101744633 A   6/2010
(Continued)

OTHER PUBLICATIONS

Extended Search Report issued Jan. 15, 2013 in European Application No. 12171386.1.

(Continued)

*Primary Examiner* — Kee M Tung
*Assistant Examiner* — Nicole Gillespie
(74) *Attorney, Agent, or Firm* — Oblon, Spivak, McClelland, Maier & Neustadt, L.L.P.

(57) ABSTRACT

An image processing system according to an embodiment includes a first image creating unit, a second image creating unit, and a display controller. The first image creating unit creates a first image by performing a rendering processing on volume data which is three-dimensional medical image data. The second image creating unit creates a second image having a different stereoscopic effect from the first image by performing the rendering processing on the volume data. The display controller that controls to display the first image and the second image in a designated region that is designated in a display surface of a display unit and a background region other than the designated region, respectively.

14 Claims, 18 Drawing Sheets

(51) Int. Cl.

| | | |
|---|---|---|
| *G02B 27/22* | (2006.01) | |
| *A61B 8/13* | (2006.01) | |
| *A61B 8/00* | (2006.01) | |
| *A61B 8/08* | (2006.01) | |
| *A61B 5/055* | (2006.01) | |
| *G06T 19/00* | (2011.01) | |
| *H04N 13/02* | (2006.01) | |
| *A61B 6/02* | (2006.01) | |
| *H04N 5/445* | (2011.01) | |
| *A61B 6/00* | (2006.01) | |
| *A61B 6/03* | (2006.01) | |

(56) References Cited

U.S. PATENT DOCUMENTS

| | | | |
|---|---|---|---|
| 2005/0289472 A1 | 12/2005 | Morita et al. | |
| 2006/0192780 A1 | 8/2006 | Lantin | |
| 2010/0040200 A1* | 2/2010 | Ema et al. | 378/98.12 |
| 2010/0201785 A1 | 8/2010 | Lantin | |
| 2011/0235066 A1* | 9/2011 | Sakuragi | 358/1.6 |

FOREIGN PATENT DOCUMENTS

| | | |
|---|---|---|
| JP | 7-271997 | 10/1995 |
| JP | 2001-128982 | 5/2001 |
| JP | 2004-40722 | 2/2004 |
| JP | 2005-86414 | 3/2005 |
| JP | 2005-322257 | 11/2005 |
| JP | 2006-25885 | 2/2006 |
| JP | 2008-259697 | 10/2008 |

OTHER PUBLICATIONS

Frank Stenicke, et al., "Interscopic User Interface Concepts for Fish Tank Virtual Reality Systems", IEEE Virtual Reality Conference, 2007, XP031080291, pp. 27-34.

Office Action issued Nov. 27, 2012 in Japanese Patent Application No. 2012-114844 (with English-language translation).

Office Action mailed Feb. 25, 2014, in Chinese Patent Application No. 201210190209.X.

* cited by examiner

LAYER 1    LAYER 2

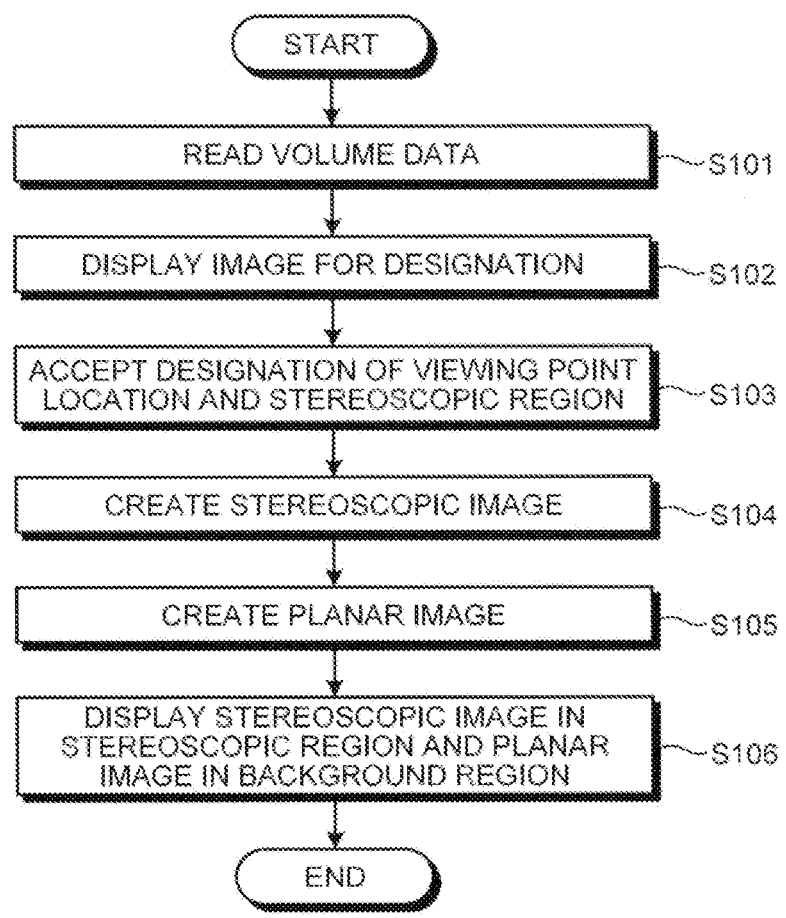

FIG.22
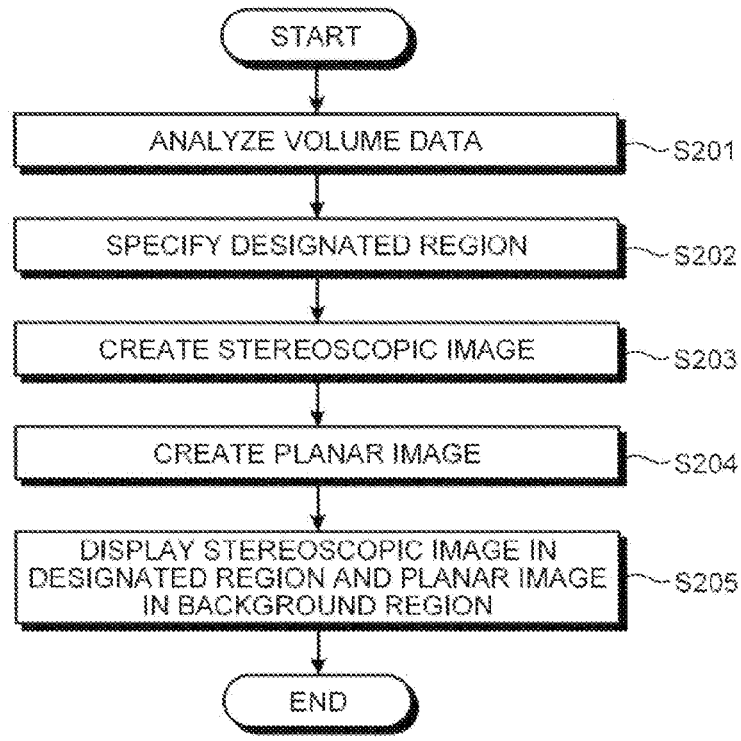
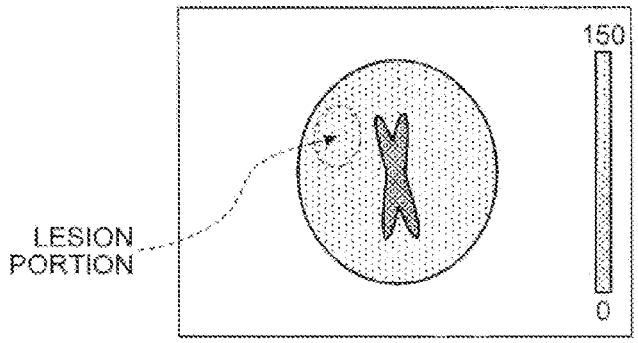
FIG.23A
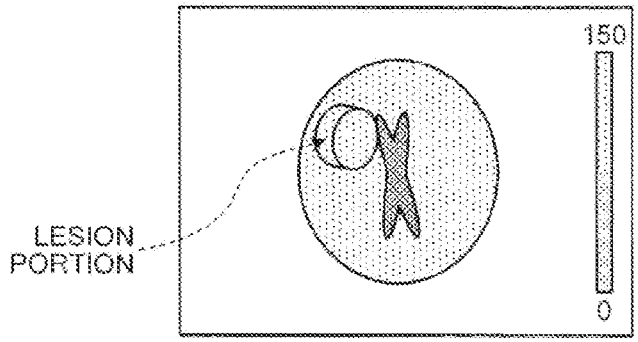
FIG.23B

IMAGE PROCESSING SYSTEM AND METHOD THEREOF

CROSS-REFERENCE TO RELATED APPLICATIONS

This application is based upon and claims the benefit of priority from Japanese Patent Application No. 2011-129368, filed on Jun. 9, 2011; the entire contents of which are incorporated herein by reference.

FIELD

Embodiments described herein relate generally to an image processing system and a method thereof.

BACKGROUND

In the related art, a monitor that stereoscopically displays a binocular disparity image captured from two viewing points using a specialized device such as stereoscopic glasses is put to practical use. Further, in recent years, a monitor that stereoscopically displays multiple disparity image (for example, nine disparity image) captured from multiple viewing points with naked eyes using a light beam controller such as a lenticular lens is put to practical use. Sometimes, two disparity images or nine disparity images that are displayed on a stereoscopically viewable monitor may be created by estimating depth information of an image captured from one viewing point and performing image processing using the estimated information.

In the meantime, as a medical diagnostic imaging apparatus such as an X-ray CT (computed tomography) apparatus, an MRI (Magnetic Resonance Imaging) apparatus, or an ultrasonic diagnostic apparatus, a apparatus that is capable of creating three-dimensional medical image data (hereinafter, referred to as volume data) is put to practical use. In the related art, the volume data created by such a medical diagnostic imaging apparatus is changed into a two-dimensional image by various image processing and then two-dimensionally displayed on a general purpose monitor. For example, the volume data created by the medical diagnostic imaging apparatus is changed into a two-dimensional image to which three-dimensional information is reflected by a volume rendering processing and then two-dimensionally displayed on a general purpose monitor.

BRIEF DESCRIPTION OF THE DRAWINGS

FIG. 15 is a flowchart illustrating processing procedures according to the first embodiment;

FIG. 22 is a flowchart illustrating processing procedures according to the third embodiment;

FIGS. 23A and 23B are views illustrating a display example according to a modification example of the third embodiment;

DETAILED DESCRIPTION

An image processing system according to the present embodiments includes a first image creating unit, a second image creating unit, and a display controller. The first image creating unit is configured to create a first image by performing a rendering processing on volume data which is three-dimensional medical image data. The second image creating unit is configured to create a second image having a different stereoscopic effect from the first image by performing the rendering processing on the volume data. The display controller is configured to control to display the first image and the second image in a designated region that is designated in a display surface of a display unit and a background region other than the designated region, respectively.

Hereinafter, with reference to the accompanying drawings, embodiments of an image processing system and an image processing method will be described. Here, terminologies to be used in the following embodiments will be described. "Disparity image group" refers to an image group that is created by moving a viewing point by a predetermined disparity angle to perform a rendering processing on volume data. That is, a "disparity image group" is configured by a plurality of "disparity images" whose viewing points are different from each other. Further, the "disparity angle" refers to an angle determined by adjacent viewing point locations among the viewing point locations set for creating the "disparity image group" and a predetermined location in a space (for example, a center of the space) specified by the volume data. Furthermore, a "disparity number" refers to the number of "disparity images" required for stereoscopically viewing through a stereoscopically viewable monitor. "Nine disparity images" which will be described below refers to a "disparity image group" configured by nine "disparity images". "Two disparity images" which will be described below refers to a "disparity image group" configured by two "disparity images".

First Embodiment

Figure 1:
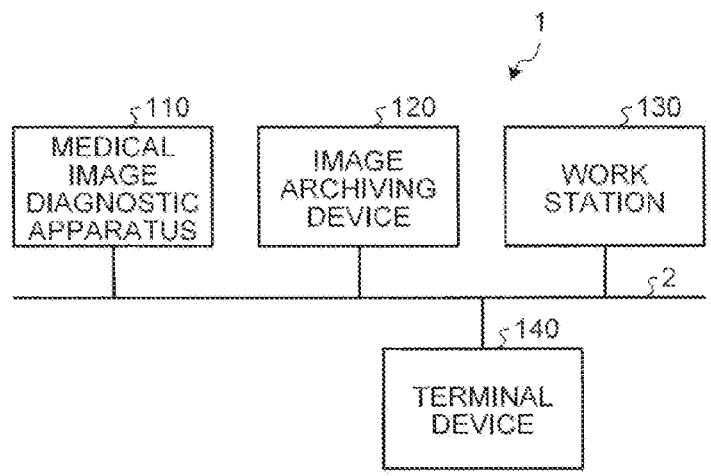
FIG. 1 is a view illustrating a configuration example of an image processing system according to a first embodiment.

First, a configuration example of an image processing system according to a first embodiment will be described. FIG. 1 is a view illustrating a configuration example of an image processing system according to the first embodiment.

As illustrated in FIG. 1, an image processing system 1 according to the first embodiment includes a medical image diagnostic apparatus 110, an image archiving device 120, a work station 130, and a terminal device 140. The devices illustrated in FIG. 1, for example, are directly or indirectly communicated with each other through an in-hospital LAN (local area network) 2 provided in a hospital. For example, when a PACS (picture archiving and communication system) is implemented into the image processing system 1, the devices receive or transmit medical images to or from each other in accordance with a DICOM (Digital Imaging and Communications in Medicine) standard.

The above-mentioned image processing system 1 creates a disparity image group from volume data which is three-dimensional medical image data created by the medical image diagnostic apparatus 110 and displays the disparity image group on a stereoscopically viewable monitor to provide a stereoscopically viewable medical image to a doctor or a laboratory technician who works in the hospital. Specifically, in the first embodiment, the work station 130 performs various image processings on the volume data to create the disparity image group. Further, the work station 130 and the terminal device 140 have the stereoscopic viewable monitor and display the disparity image group created by the work station 130 on the monitor. The image archiving device 120 archives the volume data created by the medical image diagnostic apparatus 110 and the disparity image group created by the work station 130. In other words, the work station 130 or the terminal device 140 obtains the volume data or the disparity image group from the image archiving device 120 and processes or displays the volume data or the disparity image group on the monitor. Hereinafter, each of the devices will be described in turns.

The medical image diagnostic apparatus 110 is an X-ray diagnostic apparatus, an X-ray CT (computed tomography) apparatus, an MRI (magnetic resonance imaging) apparatus, an ultrasonic diagnostic apparatus, an SPECT (single photon emission computed tomography) apparatus, a PET (positron emission computed tomography) apparatus, an SPECT-CT apparatus in which the SPECT apparatus e and the X-ray CT apparatus are integrated, a PET-CT apparatus in which the PET apparatus and the X-ray CT apparatus are integrated, or a group of the above apparatus. Further, the medical image diagnostic apparatus 110 according to the first embodiment is capable of creating three-dimensional medical image data (volume data).

Specifically, the medical image diagnostic apparatus 110 according to the first embodiment captures an object to create volume data. For example, the medical image diagnostic apparatus 110 captures the object to collect projected data or data such as an MR (magnetic resonance) signal and reconstructs medical image data on a plurality of axial surfaces along an axis of a body of the object from the collected data to create volume data. For example, the medical image diagnostic apparatus 110 reconstructs medical image data on 500 sheets of axial surfaces. The medical image data group on 500 sheets of axial surfaces is volume data. Further, the captured data of the object or the MR signal captured by the medical image diagnostic apparatus 110 may be served as volume data.

Further, the medical image diagnostic apparatus 110 according to the first embodiment transmits the created volume data to the image archiving device 120. When the volume data is transmitted to the image archiving device 120, the medical image diagnostic apparatus 110 transmits, for example, a patient ID identifying a patient, an examination ID identifying examination, a device ID identifying the medical image diagnostic apparatus 110, and a series ID identifying single capturing by the medical image diagnostic apparatus 110, as supplementary information.

The image archiving device 120 is a database that archives the medical image. Specifically, the image archiving device 120 according to the first embodiment stores volume data transmitted from the medical image diagnostic apparatus 110 in a storage unit and then archives the volume data. Further, in the first embodiment, the work station 130 creates the disparity image group from the volume data and transmits the created disparity image group to the image archiving device 120. Therefore, the image archiving device 120 stores the disparity image group transmitted from the work station 130 in the storage unit and archives the disparity image group. In the first embodiment, by using the work station 130 that is capable of archiving large quantity of images, the work station 130 and the image archiving device 120 illustrated in FIG. 1 may be integrated. In other words, in the first embodiment, the volume data or the disparity image group may be stored in the work station 130.

In the first embodiment, the volume data or the disparity image group archived in the image archiving device 120 is stored to be associated with the patient ID, the examination ID, the device ID, and the series ID. Therefore, the work station 130 or the terminal device 140 searches for the volume data or the disparity image group using the patient ID, the examination ID, the device ID, or the series ID to obtain required volume data or a disparity image group from the image archiving device 120.

The work station 130 is an image processing device that performs the image processing on the medical image. Specifically, the work station 130 according to the first embodiment performs various rendering processings on the volume data obtained from the image archiving device 120 and creates the disparity image group.

Further, the work station 130 according to the first embodiment includes a stereoscopically viewable monitor (hereinafter, stereoscopic display monitor) as a display unit. The work station 130 creates the disparity image group and displays the created disparity image group on the stereoscopic display monitor. As a result, an operator of the work station 130 may perform an operation for creating the disparity image group while checking the stereoscopically viewable medical image displayed on the stereoscopic display monitor.

The work station 130 transmits the created disparity image group to the image archiving device 120. When the disparity image group is transmitted to the image archiving device 120, the work station 130 transmits, for example, the patient ID, the examination ID, the device ID, and the series ID, as supplementary information. As supplementary information when the disparity image group is transmitted to the image archiving device 120, supplementary information concerning the disparity image group is included. The supplementary information concerning the disparity image group includes the number of disparity images (for example, "9") or a resolution of the disparity image (for example, "466×350 pixels").

The terminal device 140 is a device that allows the doctor or the laboratory technician who works in the hospital to browse the medical image. For example, the terminal device 140 includes a PC (personal computer), a tablet PC, a PDA (personal digital assistant), or a cellular phone that is operated by the doctor or the laboratory technician who works in the hospital. Specifically, the terminal device 140 according to the first embodiment includes a stereoscopic display monitor as a display unit. The terminal device 140 obtains the disparity image group from the image archiving device 120 and displays the obtained disparity image group on the stereoscopic display monitor. As a result, the doctor or the laboratory technician who is an observer may browse the stereoscopically viewable medical image.

Here, the stereoscopic display monitor included in the work station 130 or the terminal device 140 will be described. A currently most popular general purpose monitor two-dimensionally displays a two-dimensional image, but cannot stereoscopically display the two-dimensional image. If the observer wants to stereoscopically view an image on the general purpose monitor, a device that outputs an image to the general purpose monitor needs to display two disparity images that are stereoscopically viewed by the observer so as to be parallel to each other by a parallel method or an intersection method. Otherwise, a device that outputs the image on the general purpose monitor is required to display the image that are stereoscopically viewed by an observer by a complementary color method using glasses with a red color cellophane fixed on a left eye part and a blue color cellophane fixed on a right eye part.

In the meantime, the stereoscopic display monitor may allow the two disparity image (also referred to as binocular disparity image) to be stereoscopically viewed using a specialized device such as stereoscopic glasses.

Figure 2A:
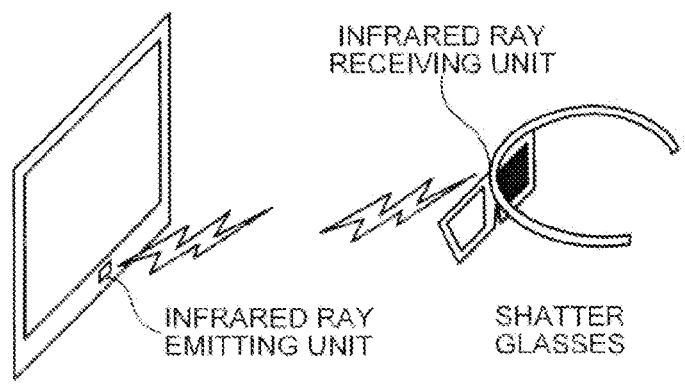
FIGS. 2A and 2B are views illustrating an example of a stereoscopic display monitor that performs stereoscopic display using a two disparity image.
Figure 2B:
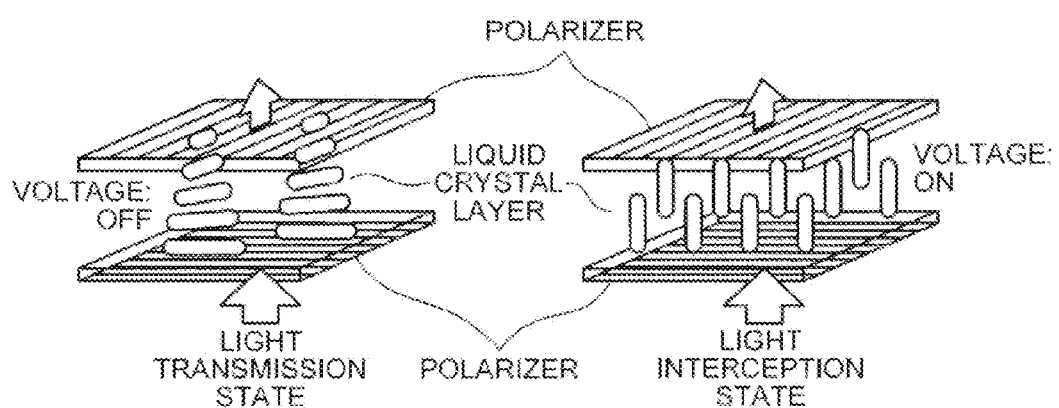

FIGS. 2A and 2B are views illustrating an example of a stereoscopic display monitor that performs stereoscopic display using a two disparity image. The example illustrated in FIGS. 2A and 2B is a stereoscopic display monitor that performs stereoscopic display using a shutter method and shutter glasses are used as stereoscopic glasses that a user may wear to watch the monitor. Such stereoscopic display monitor alternatively emits two disparity images onto a monitor. For example, the monitor illustrated in FIG. 2A alternatively emits an image for a left eye and an image for a right eye at 120 Hz. Here, as illustrated in FIG. 2A, an infrared ray emitting unit is provided on the monitor to control the emission of the infrared ray in accordance with the timing when the images are switched.

Further, the infrared ray emitted from the infrared ray emitting unit is received by an infrared ray receiving unit of the shutter glasses illustrated in FIG. 2A. Shatters are fixed on left and right frames of the shatter glasses and the shatter glasses alternatively switches a light transmission state and a light interception state of the right and left shatters in accordance with a timing when the infrared ray receiving unit receives the infrared ray. Hereinafter, the switching processing of the light transmission state and the light interception state in the shatter will be described.

Each of the shatters, as illustrated in FIG. 2B, includes a light incident side polarizer, a light emission side polarizer, and liquid crystal layer between the light incident side polarizer and the light emission side polarizer. The light incident side polarizer and the light emission side polarizer, as illustrated in FIG. 2B are orthogonal to each other. Here, as illustrated in FIG. 2B, in an "off" state where voltage is not applied, light that passes through the light incident side polarizer rotates at 90 degree by action of the liquid crystal layer and then transmits the light emission side polarizer. In other words, a shutter to which voltage is not applied becomes a light transmission state.

In the meantime, as illustrated in FIG. 2B, in an "on" state where voltage is applied, the polarization rotation effect by liquid crystal molecules of the liquid crystal layer disappears, so that the light that passes through the light incident side polarizer is blocked by the light emission side polarizer. In other words, a shutter to which voltage is applied becomes a light interception state.

For example, the infrared ray emitting unit emits the infrared ray during a period when an image for a left eye is displayed on the monitor. Therefore, the infrared ray receiving unit applies voltage to the right eye shatter without applying voltage to the left eye shatter during a period when the infrared ray is received. By doing this, as illustrated in FIG. 2A, the right eye shatter becomes a light interception state and the left eye shatter becomes a light transmission state, so that the image for a left eye is incident onto a left eye of the observer. In the meantime, the infrared ray emitting unit stops emitting the infrared ray during a period when an image for a right eye is displayed on the monitor. Therefore, the infrared ray receiving unit applies voltage to the left eye shatter without applying voltage to the right eye shatter during a period when the infrared ray is not received. By doing this, the left eye shatter becomes a light interception state and the right eye shatter becomes a light transmission state, so that the image for a right eye is incident onto a right eye of the observer. As described above, the stereoscopic display monitor illustrated in FIGS. 2A and 2B simultaneously switches the image which is displayed on the monitor and the status of the shatter to display an image that is stereoscopically viewed by the observer. As the stereoscopic display monitor that is stereoscopically viewable the two disparity image, a monitor that adopts a polarization glass method is also known in addition to the above-described shutter method.

Further, as the stereoscopic display monitor that is put to practical use in recent years, a polarization controller such as a lenticular lens is used to allow an observer to stereoscopically view, for example, multiple disparity images such as nine disparity images with naked eyes. Such stereoscopic display monitor is stereoscopically viewable by a binocular disparity and is stereoscopically viewable by motion parallax that a video to be observed is also changed in accordance with movement of the viewing point of the observer.

Figure 3:
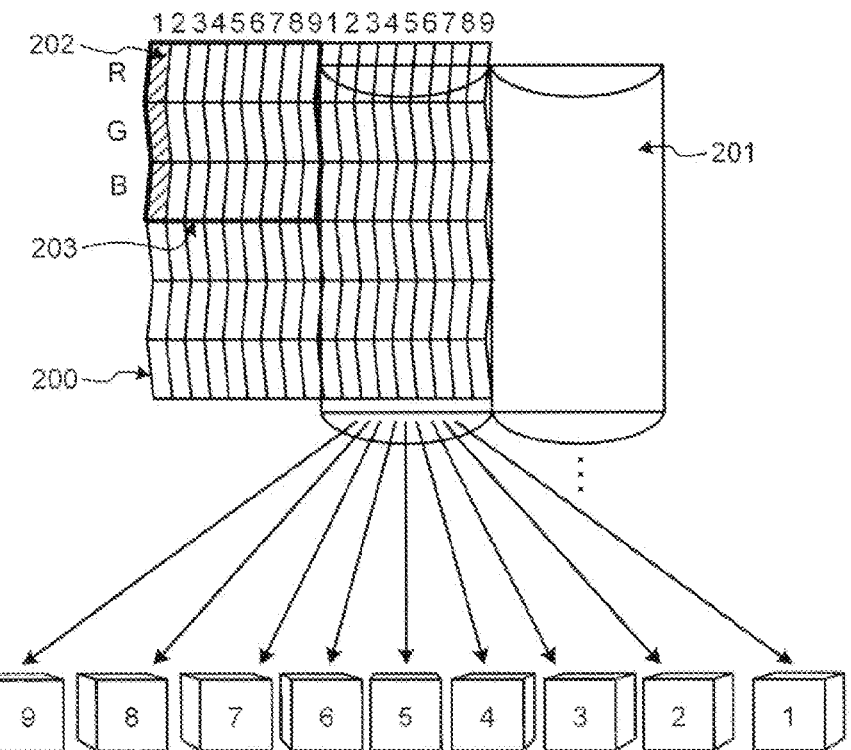
FIG. 3 is a view illustrating an example of a stereoscopic display monitor that stereoscopically displays nine disparity image.

FIG. 3 is a view illustrating an example of a stereoscopic display monitor that stereoscopically displays nine disparity images. In the stereoscopic display monitor illustrated in FIG. 3, a light ray controller is disposed on a front surface of a flat display surface 200 such as a liquid crystal panel. For example, in the stereoscopic display monitor illustrated in FIG. 3, as the light ray controller, a perpendicular lenticular sheet 201 whose optical opening extends in a perpendicular direction is fixed onto the front surface of the display surface 200. Further, in the example illustrated in FIG. 3, a convex portion of the perpendicular lenticular sheet 201 is attached so as to be served as the front surface. However, the convex portion of the perpendicular lenticular sheet 201 may be attached so as to be opposite to the display surface 200.

On the display surface 200, as illustrated in FIG. 3, pixels 202 of which an aspect ratio is 3:1 and on which three red (R), green (G), and blue (B) sub pixels are arranged in a longitudinal direction are arranged in a matrix. The stereoscopic display monitor illustrated in FIG. 3 converts the nine disparity images configured by nine images into an intermediate image which is arranged in a predetermined format (for example, in a lattice) and then outputs the images to the display surface 200. That is, the stereoscopic display monitor illustrated in FIG. 3 outputs the nine pixels so as to allocate nine pixels which are at the same position in the nine disparity images into nine rows of pixels 202. The nine rows of pixels 202 become a unit pixel group 203 that simultaneously displays nine images having different viewing point locations.

The nine disparity images that are simultaneously output as the unit pixel group 203 on the display surface 200, for example, are radiated as parallel light by an LED (light emitting diode) backlight and radiated in multiple directions by the perpendicular lenticular sheet 201. The light of the pixels of the nine disparity images is radiated in the multiple directions so that the light entering the right eye and the left eye of the observer is changed in connection with the position (position of the viewing point) of the observer. In other words, due to the angle that is watched by the observer, a disparity angle of the disparity image entering the right eye is different from a disparity angle of the disparity image entering the left eye. Therefore, the observer, for example, may stereoscopically view the capturing target in nine locations illustrated in FIG. 3. Further, the observer may stereoscopically view the target in front of the capturing target in, for example, a position of "5" illustrated in FIG. 3. Further, in positions other than "5" illustrated in FIG. 3, the observer may stereoscopically view the target in a status that the direction of the capturing target is changed. Further, the stereoscopic display monitor illustrated in FIG. 3 is just an example. The stereoscopic display monitor that displays the nine disparity images, as illustrated in FIG. 3, may be horizontal stripe liquid crystals of "RRR . . . , GGG . . . , BBB . . . " or vertical stripe liquid crystals of "RGBRGB . . . ". Further, as illustrated in FIG. 3, the stereoscopic display monitor illustrated in FIG. 3 may use a vertical lens method in which the lenticular sheet is vertical or an oblique lens method in which the lenticular sheet is oblique.

So far, a configuration example of the image processing system 1 according to the first embodiment was briefly described. Further, the application of the above-described image processing system 1 is not limited to the case where the PACS is introduced. For example, even when an electronic chart system that manages an electronic chart having a medical image attached thereto is introduced, the image processing system 1 is also applied in the same manner. In this case, the image archiving device 120 is a database for archiving the electronic chart. For example, even when an HIS (hospital information system) and an RIS (radiology information system) are introduced, the image processing system 1 is applied in the same manner. The image processing system 1 is not limited to the above-described configuration example. Functions or contributions of the devices may be appropriately changed in accordance with operational forms.

Figure 4:
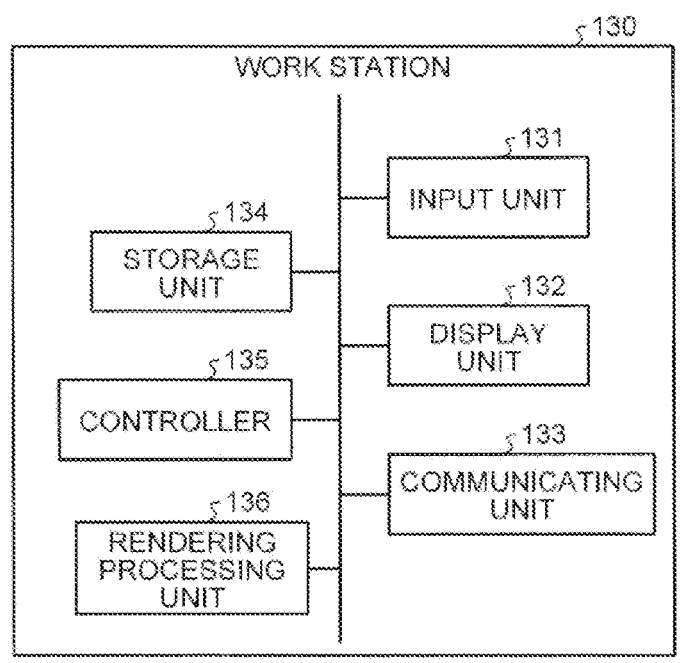
FIG. 4 is a view illustrating a configuration example of a work station according to the first embodiment.

Next, the configuration example of the work station according to the first embodiment will be described with reference to FIG. 4. FIG. 4 is a view illustrating a configuration example of the work station according to the first embodiment.

The work station 130 according to the first embodiment is a high performance computer suitable for image processing, and as illustrated in FIG. 4, includes an input unit 131, a display unit 132, a communicating unit 133, a storage unit 134, a controller 135, and a rendering processing unit 136. Hereinafter, even though it will be described that the work station 130 is a high performance computer that is suitable for image processing, the work station 130 is not limited thereto, but may be an information processing device. For example, the work station 130 may be a personal computer.

The input unit 131 is a mouse, a keyboard, or a track ball and accepts inputs for various manipulations for the work station 130 from an operator. For example, the input unit 131 according to the first embodiment accepts an input of information for obtaining volume data which is a target for a rendering processing from the image archiving device 120. For example, the input unit 131 accepts inputs such as the patient ID, the examination ID, the device ID, or the series ID. Further, for example, the input unit 131 according to the first embodiment accepts an input of a condition (hereinafter, rendering condition) for the rendering processing.

The display unit 132 is a liquid crystal panel as the stereoscopic display monitor and displays various information. For example, the display unit 132 according to the first embodiment displays a GUI (graphical user interface) for accepting various manipulations from the operator and the disparity image group. The communicating unit 133 is an NIC (network interface card) and communicates with other devices.

The storage unit 134 is a hard disk or a semiconductor memory device and stores various information. For example, the storage unit 134 according to the first embodiment stores volume data obtained from the image archiving device 120 through the communicating unit 133. The storage unit 134 according to the first embodiment stores volume data which is being rendered and the disparity image group created by the rendering processing.

The controller 135 is an electronic circuit such as a CPU (central processing unit) or an MPU (micro processing unit) or an integrated circuit such as an ASIC (application specific integrated circuit) or an FPGA (field programmable gate array) and controls the whole work station 130.

For example, the controller 135 according to the first embodiment controls the display unit 132 to display a GUI and the disparity image group. Further, for example, the controller 135 controls to transmit/receive the volume data and the disparity image group to/from the image archiving device 120 through the communicating unit 133. Further, for example, the controller 135 controls the rendering processing of the rendering processing unit 136. Further, for example, the controller 135 controls to read the volume data from the storage unit 134 and store the disparity image group in the storage unit 134.

The rendering processing unit 136 performs various rendering processings on the volume data obtained from the image archiving device 120 under the control of the controller 135 and creates the disparity image group. Specifically, the rendering processing unit 136 according to the first embodiment reads the volume data from the storage unit 134 and performs pre-processing on the volume data. Next, the rendering processing unit 136 performs a volume rendering processing on the pre-processed volume data to create the disparity image group. Subsequently, the rendering processing unit 136 creates a two-dimensional image in which various information (a scale, a patient name, or an examination item) is represented and superposes the various information with each disparity image group to create a two-dimensional image for outputting. The rendering processing unit 136 stores the created disparity image group and two-dimensional image for outputting in the storage unit 134. In the first embodiment, the rendering processing refers to all image processings that are performed on the volume data. Further, the volume rendering processing refers to a processing of creating a two-dimensional image to which three-dimensional information is reflected, out of the rendering processing. The rendering processing includes a surface rendering processing in addition to the volume rendering processing. The volume rendering processing is a method of creating a two-dimensional image to which three-dimensional information is directly reflected from the volume data. In contrast, the surface rendering processing is a method of extracting data, which is a target, from the volume data to build a model and create a two-dimensional image to which three-dimensional information is reflected based on the built model. In the first embodiment, an example that uses the volume rendering processing method is described. However, the embodiment is not limited thereto, but the surface rendering processing method may be used.

Figure 5:
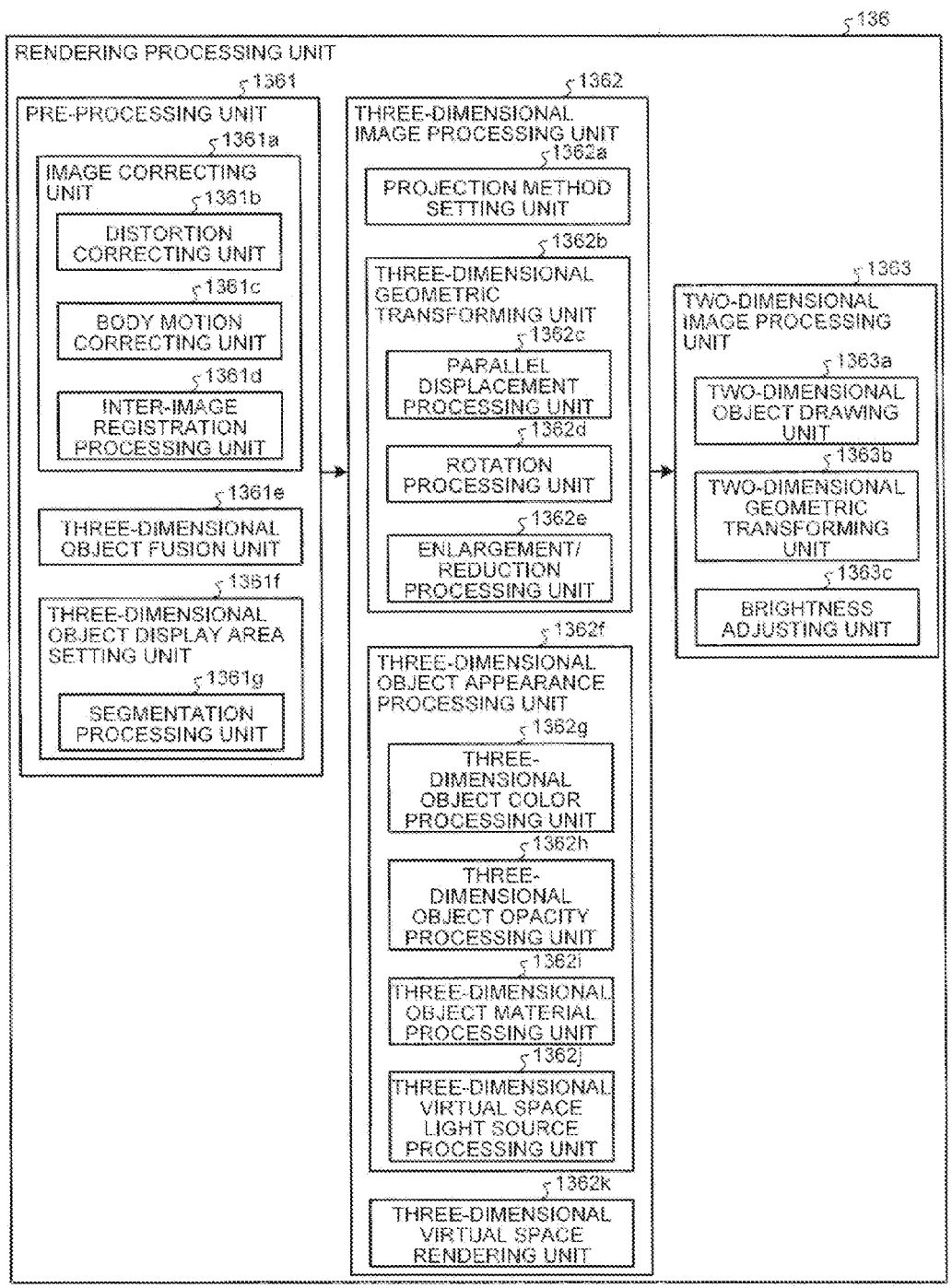
FIG. 5 is a view illustrating a configuration example of a rendering processing unit illustrated in FIG. 4.

FIG. 5 is a view illustrating a configuration example of a rendering processing unit illustrated in FIG. 4. As illustrated in FIG. 5, the rendering processing unit 136 includes a pre-processing unit 1361, a three-dimensional image processing unit 1362, and a two-dimensional image processing unit 1363. The pre-processing unit 1361 performs a pre-processing on volume data, the three-dimensional image processing unit 1362 creates a disparity image group from the pre-processed volume data, and the two-dimensional image processing unit 1363 creates a two-dimensional image for outputting in which various information is superposed with the disparity image group. Hereinafter, each unit will be described in turns.

The pre-processing unit 1361 is a processing unit that performs various pre-processings when the rendering processing is performed on the volume data, and includes an image correcting unit 1361*a*, a three-dimensional object fusion unit 1361*e*, and a three-dimensional object display area setting unit 1361*f*.

The image correcting unit 1361*a* is a processing unit that performs image correction when two kinds of volume data are processed as single volume data. As illustrated in FIG. 5, the image correcting unit 1361*a* includes a distortion correcting unit 1361*b*, a body motion correcting unit 1361*c*, and an inter-image registration processing unit 1361*d*. For example, the image correcting unit 1361*a* corrects images when volume data of a PET image and volume data of an X-ray CT image created by the PET-CT device are processed as single volume data. Alternatively, the image correcting unit 1361*a* corrects images when volume data of a T1 weighted image and volume data of a T2 weighted image created by an MRI device are processed as single volume data.

The distortion correcting unit 1361*b* corrects distortion of individual volume data caused by the collection condition when the data is collected by the medical image diagnostic apparatus 110. Further, the body motion correcting unit 1361*c* corrects the movement caused by the body motion of a subject occurring when data used for creating individual volume data is collected. The inter-image registration processing unit 1361*d* performs registration between two volume data on which the correcting processing is performed by the distortion correcting unit 1361*b* and the body motion correcting unit 1361*c* using, for example, a cross-correlation method.

The three-dimensional object fusion unit 1361*e* fuses a plurality of volume data on which the registration is performed by the inter-image registration processing unit 1361*d*. The processings of the image correcting unit 1361*a* and the three-dimensional object fusion unit 1361*e* are omitted when the rendering processing is performed on the single volume data.

The three-dimensional object display area setting unit 1361*f* is a processing unit that sets a display area corresponding to a display target organ designated by the operator, and includes a segmentation processing unit 1361*g*. The segmentation processing unit 1361*g* is a processing unit that extracts an organ such as a heart, a lung, or a blood vessel designated by the operator based on, for example, a value of a pixel of volume data (value of a voxel) by a region expansion method.

The segmentation processing unit 1361*g* does not perform the segmentation processing when the display target organ is not designated by the operator. Further, when a plurality of display target organs are designated by the operator, the segmentation processing unit 1361*g* extracts the plurality of organs. The processing of the segmentation processing unit 1361*g* may be re-performed in accordance with the fine adjustment request of the operator who refers to the rendering image.

The three-dimensional image processing unit 1362 performs the volume rendering processing on the volume data onto which the pre-processing is performed by the pre-processing unit 1361. As the processing unit that performs the volume rendering processing, the three-dimensional image processing unit 1362 includes a projection method setting unit 1362*a*, a three-dimensional geometric transforming unit 1362*b*, a three-dimensional object appearance processing unit 1362*f*, and a three-dimensional virtual space rendering unit 1362*k*.

The projection method setting unit 1362*a* determines a projection method for creating a disparity image group. For example, the projection method setting unit 1362*a* determines whether the volume rendering processing is performed by a parallel projection method or a perspective projection method.

The three-dimensional geometric transforming unit 1362*b* is a processing unit that determines information for three-dimensionally and geometrically transforming the volume data onto which the volume rendering processing is performed, and includes a parallel displacement processing unit 1362*c*, a rotation processing unit 1362*d*, and an enlargement/reduction processing unit 1362*e*. The parallel displacement processing unit 1362*c* is a processing unit that determines the amount of displacement by which the volume data moves in parallel when the viewing point location is moved in parallel when the volume rendering processing is performed. The rotation processing unit 1362*d* is a processing unit that determines the amount of displacement by which the volume data moves rotationally when the viewing point location is rotationally moved when the volume rendering processing is performed. The enlargement/reduction processing unit 1362*e* is a processing unit that determines an enlargement ratio or a reduction ratio of the volume data when the enlargement or reduction of the disparity image group is required.

The three-dimensional object appearance processing unit 1362*f* includes a three-dimensional object color processing unit 1362*g*, a three-dimensional object opacity processing unit 1362*h*, a three-dimensional object material processing unit 1362*i*, and a three-dimensional virtual space light source processing unit 1362*j*. The three-dimensional object appearance processing unit 1362*f* uses the above-mentioned processing units to determine a display status of the disparity image group to be displayed, for example, in response to the request of the operator.

The three-dimensional object color processing unit 1362*g* is a processing unit that determines a color to be colored in each of the regions segmented in the volume data. The three-dimensional object opacity processing unit 1362h is a processing unit that determines opacity of each of the voxels that configures each of the regions segmented in the volume data. A region behind a region in the volume data whose opacity is "100%" is not represented in the disparity image group. A region in the volume data whose opacity is "0%" is not represented in the disparity image group.

The three-dimensional object material processing unit 1362i is a processing unit that determines a texture of each of the regions segmented in the volume data to adjust the texture when the region is represented. The three-dimensional virtual space light source processing unit 1362j is a processing unit that determines the position of a virtual light source to be disposed in a three-dimensional virtual space or the types of the virtual light when the volume rendering processing is performed on the volume data. The types of virtual light source include a light source that irradiates a parallel light beam from infinity or a light source that irradiates a radial light beam from the viewing point.

The three-dimensional virtual space rendering unit 1362k performs a volume rendering processing on the volume data to create the disparity image group. If necessary, when the volume rendering processing is performed, the three-dimensional virtual space rendering unit 1362k uses various information determined by the projection method setting unit 1362a, the three-dimensional geometric transforming unit 1362b, and the three-dimensional object appearance processing unit 1362f.

Here, the volume rendering processing by the three-dimensional virtual space rendering unit 1362k is performed in accordance with the rendering condition. For example, the rendering condition includes the "parallel projection method" or the "perspective projection method". Further, for example, the rendering condition is "viewing point location and disparity angle of a basis". Further, for example, the rendering condition is "parallel displacement of the viewing point location", "rotational displacement of the viewing point location", "enlargement of the disparity image group", and "reduction of the disparity image group". Further, for example, the rendering condition is also "color to be colored", "transmittance", "texture", "position of the virtual light source", and "types of the virtual light source". The above-mentioned rendering conditions are considered to be accepted from the operator through the input unit 131 or initially set. In any case, the three-dimensional virtual space rendering unit 1362k accepts the rendering condition from the controller 135 and performs the volume rendering processing on the volume data in accordance with the rendering condition. In this case, the above-mentioned projection method setting unit 1362a, the three-dimensional geometric transforming unit 1362b, and the three-dimensional object appearance processing unit 1362f determine various required information in accordance with the rendering condition so that the three-dimensional virtual space rendering unit 1362k uses the determined various information to create the disparity image group.

Figure 6:
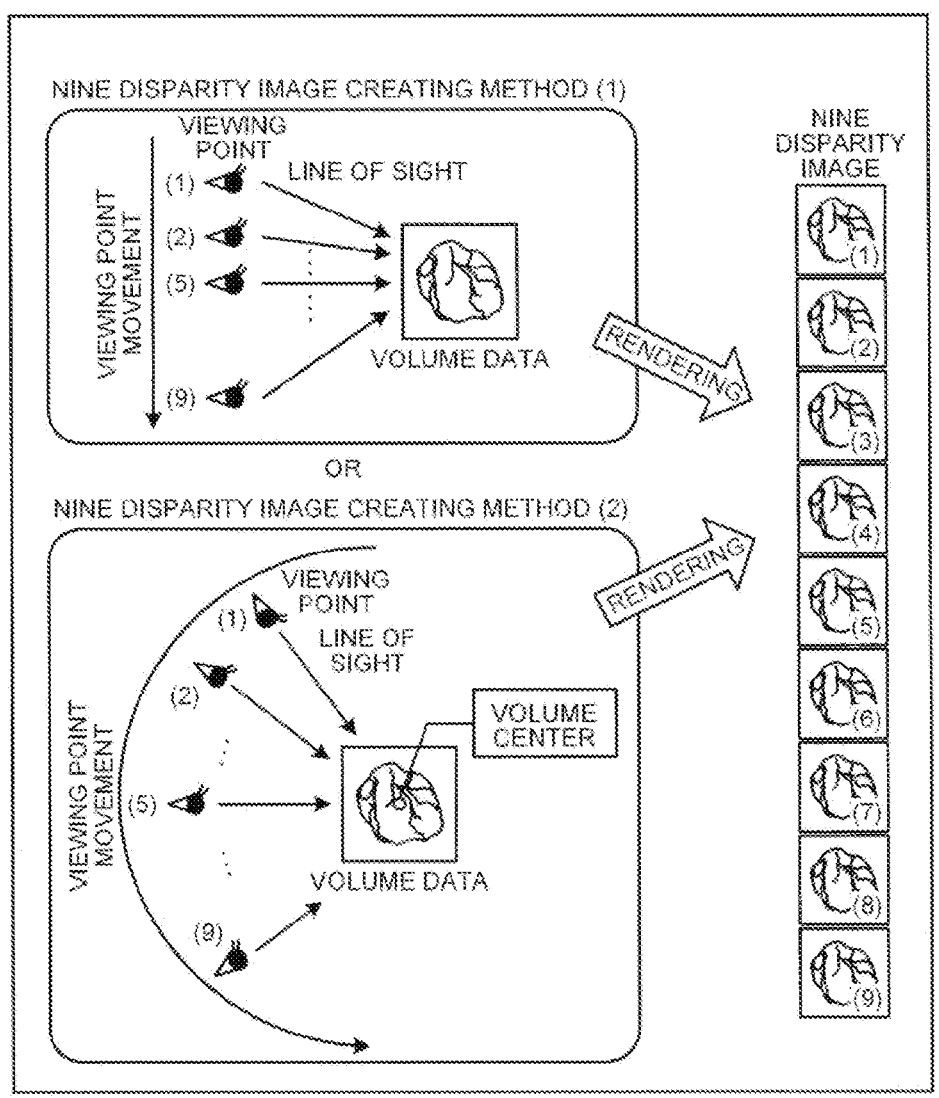
FIG. 6 is a view illustrating an example of a volume rendering processing according to the first embodiment.

FIG. 6 is a view illustrating an example of a volume rendering processing according to the first embodiment. For example, the three-dimensional virtual space rendering unit 1362k, as illustrated in "nine disparity image creating method (1)" of FIG. 6, accepts the parallel projection method as the rendering condition and accepts the viewing point location (5) and the disparity angle "1 degree" of the basis. In this case, the three-dimensional virtual space rendering unit 1362k moves the location of the viewing point to (1) to (9) in parallel so that the interval of the disparity angles is "one degree", thereby creating nine disparity images whose disparity angles (angle between lines of sight) are varied by one degree by the parallel projection method. When the parallel projection method is performed, the three-dimensional virtual space rendering unit 1362k sets a light source that irradiates a parallel light beam from the infinity along the line of sight.

Alternatively, the three-dimensional virtual space rendering unit 1362k, as illustrated in "nine disparity image creating method (2)" of FIG. 6, accepts the perspective projection method as the rendering condition and receives the viewing point location (5) and the disparity angle "1 degree" of the basis. In this case, the three-dimensional virtual space rendering unit 1362k rotationally moves the location of the viewing point to (1) to (9) such that an interval of disparity angles around the center (gravity center) of the volume data is "one degree", thereby creating nine disparity images whose viewing angles are varied by one degree by the perspective projection method. Further, if the perspective projection method is performed, the three-dimensional virtual space rendering unit 1362k sets a point light source or a surface light source that three-dimensionally and radially irradiates light with respect to the line of sight in each of the viewing points. Further, if the perspective projection method is performed, the viewing points (1) to (9) may be moved in parallel depending on the rendering condition.

The three-dimensional virtual space rendering unit 1362k may set a light source that two-dimensionally and radially irradiates light with respect to the line of sight in the longitudinal direction of the volume rendering image to be displayed and irradiates the parallel light beam from the infinity along the line of sight in the lateral direction of the volume rendering image to be displayed, thereby performing the volume rendering process using both the parallel projection method and the perspective projection method.

The nine disparity images created as described above are the disparity image group. In the first embodiment, the nine disparity images are transformed into intermediate images that are arranged in a predetermined format (for example, in a lattice) by the controller 135 and then output to the display unit 132 serving as the stereoscopic display monitor. Accordingly, an operator of the work station 130 may perform an operation for creating the disparity image group while checking the stereoscopically viewable medical image displayed on the stereoscopic display monitor.

Further, in the example of FIG. 6, as the rendering condition, the projection method and the viewing point location and the disparity angle of the basis are accepted. However, similarly, if other conditions are received as the rendering condition, the three-dimensional virtual space rendering unit 1362k creates the disparity image group while reflecting the individual rendering conditions.

The three-dimensional virtual space rendering unit 1362k also has a function of performing an MPR (multi planer reconstruction) method to reconstruct an MPR image from the volume data in addition to the volume rendering. The three-dimensional virtual space rendering unit 1362k also has a function of performing "curved MPR" and a function of performing "intensity projection".

Continuously, the disparity image group created from the volume data by the three-dimensional image processing unit 1362 becomes an underlay. Therefore, an overlay in which various information (the scale, the patient name, or the examination item) is represented is superposed with the underlay to be a two-dimensional image for outputting. The two-dimensional image processing unit 1363 is a processing unit that performs the image processing on the overlay and the underlay to create the two-dimensional image for outputting, and includes, as illustrated in FIG. 5, a two-dimensional object drawing unit 1363a, a two-dimensional geometric transforming unit 1363b, and a brightness adjusting unit 1363c. For example, the two-dimensional image processing unit 1363 superposes one overlay with each of the nine disparity images (underlay) to create nine two-dimensional images for outputting in order to reduce the load required for the creating processing of the two-dimensional image for outputting.

The two-dimensional object drawing unit 1363a is a processing unit that draws the various information represented in the overlay and the two-dimensional geometric transforming unit 1363b is a processing unit that moves in parallel or rotationally moves the position of the various information represented in the overlay and expands or reduces the various information represented in the overlay.

The brightness adjusting unit 1363c is a processing unit that performs the brightness transformation processing. For example, the brightness adjusting unit 1363c is a processing unit that adjusts the brightness of the overlay or the underlay in response to a parameter for the image processing such as a gray scale, a window width (WW), or a window level (WL) of the stereoscopic display monitor of an outputting destination.

The two-dimensional image for outputting created as described above is stored in the storage unit 134 by, for example, the controller 135 and then transmitted to the image archiving device 120 through the communicating unit 133. For example, when the terminal device 140 obtains the two-dimensional image for outputting from the image archiving device 120, transforms the two-dimensional image for outputting into the intermediate image that is arranged in a predetermined format (for example, in a lattice) and then displays the image on the stereoscopic display monitor, the doctor or the laboratory technician who is an observer may browse a stereoscopically viewable medical image in a status where the various information (the scale, the patient name, or the examination item) is represented.

The work station 130 according to the embodiment controls to create a first image and a second image having different stereoscopic effect from the first image and display the first image in any one of a designated region designated in the display surface of the stereoscopic display monitor and a background region other than the designated region and the second image in the other region. For example, the work station 130 according to the first embodiment controls to superpose a stereoscopically viewable image (hereinafter, referred to as a stereoscopic image) which is the first image and a planar image which is the second image and display the stereoscopic image in any one of the designated region designated in the display surface of the stereoscopic display monitor and the background region other than the designated region and the planar image in the other region. The stereoscopic image and the planar image are images having different stereoscopic effects.

As described above, the stereoscopic display monitor of the work station 130 may display the stereoscopic image by displaying the disparity image group having a predetermined disparity number. However, the stereoscopic display monitor may also display a planar image by displaying a plurality of same images in the disparity image group. For example, the stereoscopic display monitor according to the first embodiment, as illustrated in FIG. 3, may display the stereoscopic image by dividing each of the nine pixels which are at the same position in the nine disparity images into nine rows of pixels 202 to be output. However, the planar image may be displayed by allocating one pixel among the nine pixels into all pixels 202 of nine rows to be output.

As described above, the two-dimensional image group for outputting is created by superposing the disparity image group as the underlay with the various information as the overlay. Hereinafter, the "stereoscopic image" or the "disparity image group" may refer to a disparity image group before various information is superposed and a two-dimensional image group for outputting after the various information is superposed. Similarly, the "planar image" or the "same image group" may refer to a same image group before the various information is superposed and a two-dimensional image group for outputting after the various information is superposed. In other words, after the "stereoscopic image" as the disparity image group and the "planar image" as the same image group are superposed with each other, the various information may be superposed therewith. Further, the "stereoscopic image" and the "planar image" superposed with the various information may be superposed. Further, since the superposition of the various information may be arbitrarily changed in accordance with the operational forms, the description thereof will be omitted.

Figure 7:
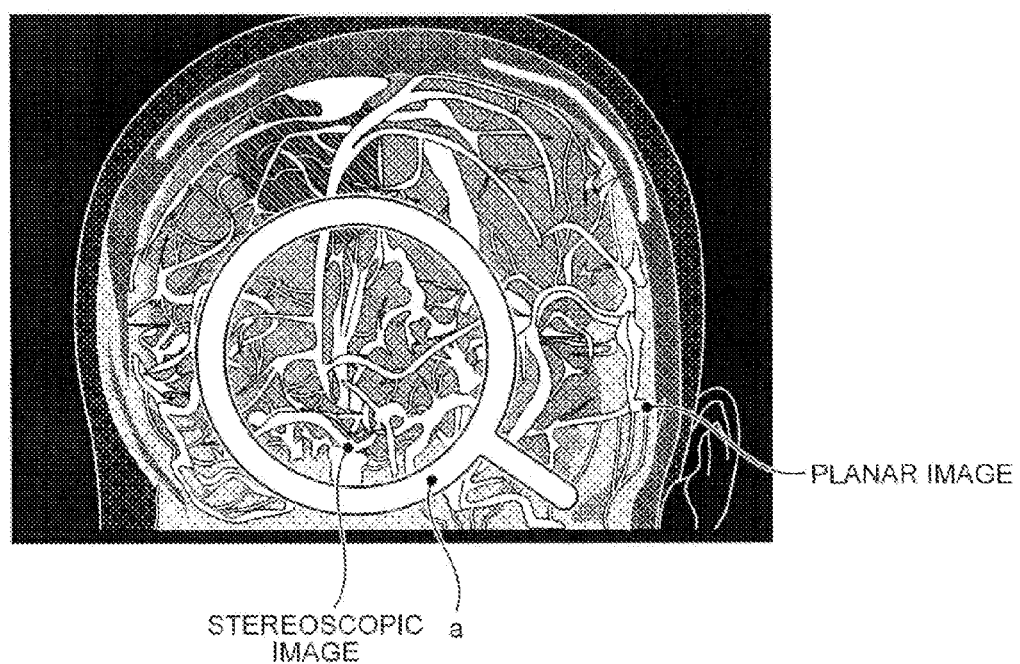
FIG. 7 is a view illustrating a display example according to the first embodiment.
Figure 8:
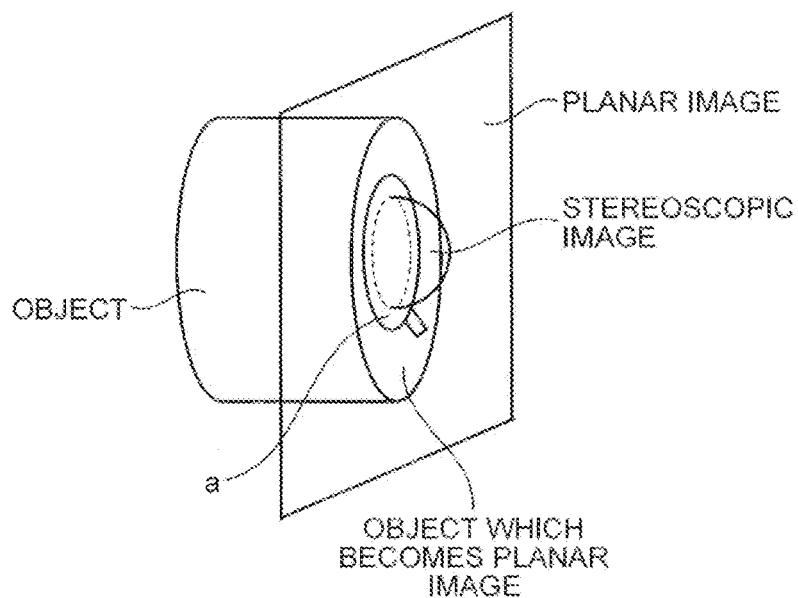
FIG. 8 is a view illustrating a display example according to the first embodiment.

FIGS. 7 and 8 are views illustrating a display example according to the first embodiment. In FIG. 7, a circular region indicated by a magnifier a indicates a designated region designated by an operator of the work station 130. As illustrated in FIG. 7, the work station 130 displays the stereoscopic image in the designated region and the planar image in the background region. Conceptually, as illustrated in FIG. 8, a stereoscopic image having a stereoscopic effect is displayed in the circular region indicated by the magnifier a and an object which becomes a planar image is displayed in the background region other than the circular region.

As described above, the work station 130 according to the first embodiment displays the stereoscopic image not only in the entire display surface in the display surface, but also only in a part of the region. The stereoscopic image has some drawbacks in that the observer may get high stress and it is difficult to focus the entire stereoscopic image. However, if the stereoscopic image is displayed only in a part of the region, the stress may be reduced, and a desired region may be focused.

Figure 9:
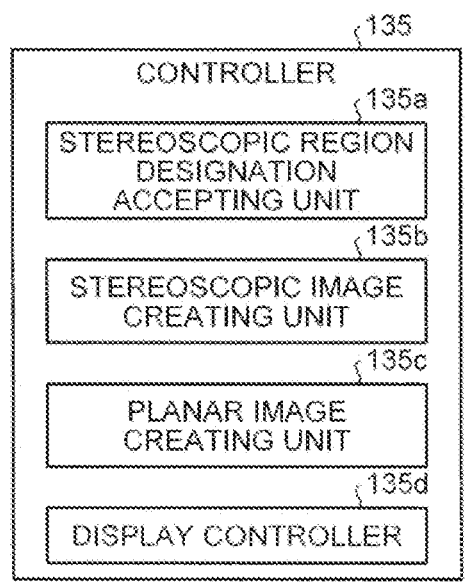
FIG. 9 is a view illustrating a configuration example of a controller according to the first embodiment.

The above-described display may be achieved by the cooperation of the controller 135, the rendering processing unit 136, and the display unit 132 in the work station 130 according to the first embodiment. FIG. 9 is a view illustrating a configuration example of the controller 135 according to the first embodiment. As illustrated in FIG. 9, the controller 135 according to the first embodiment includes a stereoscopic region designation accepting unit 135a, a stereoscopic image creating unit 135b, a planar image creating unit 135c, and a display controller 135d.

The stereoscopic region designation accepting unit 135a accepts the designation of the designated region (hereinafter, referred to as stereoscopic region) displaying the viewing point location and the stereoscopic image from the operator through the input unit 131. Specifically, the stereoscopic region designation accepting unit 135a reads the volume data from the storage unit 134, performs the volume rendering processing on the read volume data by the rendering processing unit 136, and creates a two-dimensional image (hereinafter, referred to as an image for designating) for accepting the designation of the viewing point location and the stereoscopic region. Next, the stereoscopic region designation accepting unit 135a displays the created image for designating on the display unit 132 and accepts the designation of the viewing point location and the stereoscopic region on the image for designating. Therefore, the stereoscopic region designation accepting unit 135a transmits the accepted viewing point position and stereoscopic region to the stereoscopic image creating unit 135b, and the planar image creating unit 135c.

For example, the stereoscopic region designation accepting unit 135a displays a tool of the magnifier a illustrated in FIG. 7 on the image for designating. Further, the tool of the magnifier a may be enlarged or reduced and moved on the display surface of the display unit 132 in response to the manipulation of a mouse which is the input unit 131. Therefore, the stereoscopic region designation accepting unit 135a accepts the circular region indicated by the magnifier a that is manipulated by the mouse as the stereoscopic region. Further, the designation of the stereoscopic region is not limited to the tool of the magnifier a. Similarly to the usual designation of a region of interest, the designation of the stereoscopic region may be a tool of a circular ROI (region of interest) or a polygon ROI.

The object that is represented in the image for designating is rotatable in the display surface of the display unit 132 in response to the manipulation of the mouse which is the input unit 131. Further, the viewing point location is, for example, perpendicular to the display surface. Therefore, for example, the stereoscopic region designation accepting unit 135a accepts a direction perpendicular to the image for designating, which is displayed on the display surface when the designation of the stereoscopic region is accepted, as the viewing point location.

The stereoscopic image creating unit 135b creates the stereoscopic image. Specifically, the stereoscopic image creating unit 135b uses the viewing point location and the stereoscopic region accepted from the stereoscopic region designation accepting unit 135a and the other rendering conditions to perform the volume rendering processing on the volume data read from the storage unit 134 by the rendering processing unit 136 to create the stereoscopic image group. The stereoscopic image creating unit 135b transmits the created stereoscopic image group to the display controller 135d. As the other rendering conditions, a predetermined condition may be used.

Figure 10:
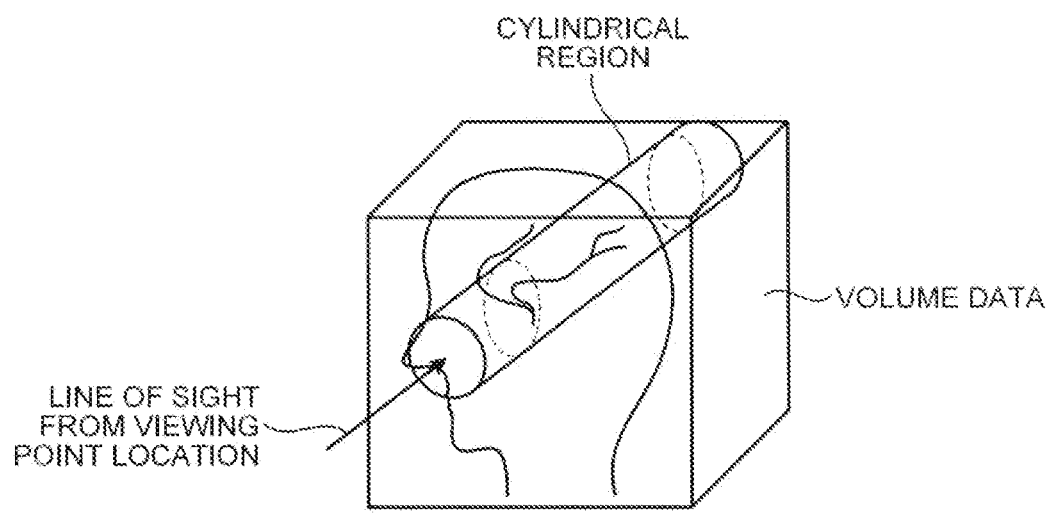
FIG. 10 is a view illustrating a stereoscopic image creating processing according to the first embodiment.
Figure 11:
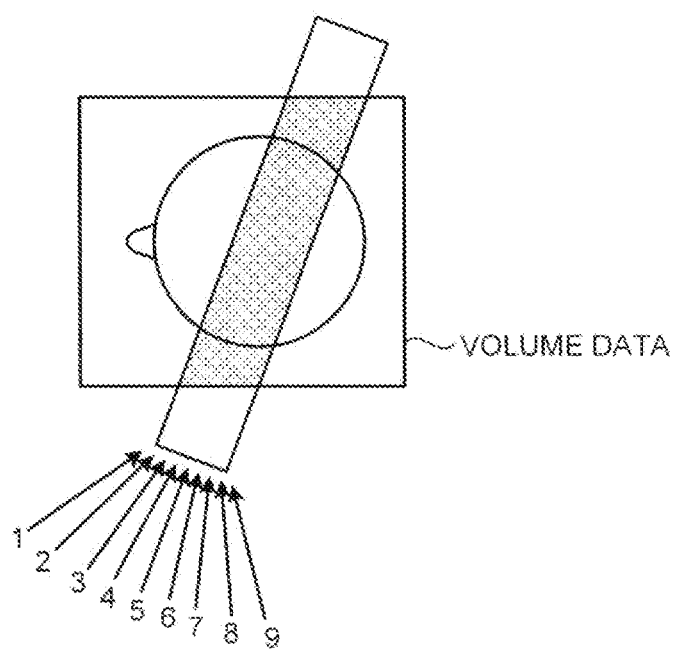
FIG. 11 is a view illustrating a stereoscopic image creating processing according to the first embodiment.
Figure 12:
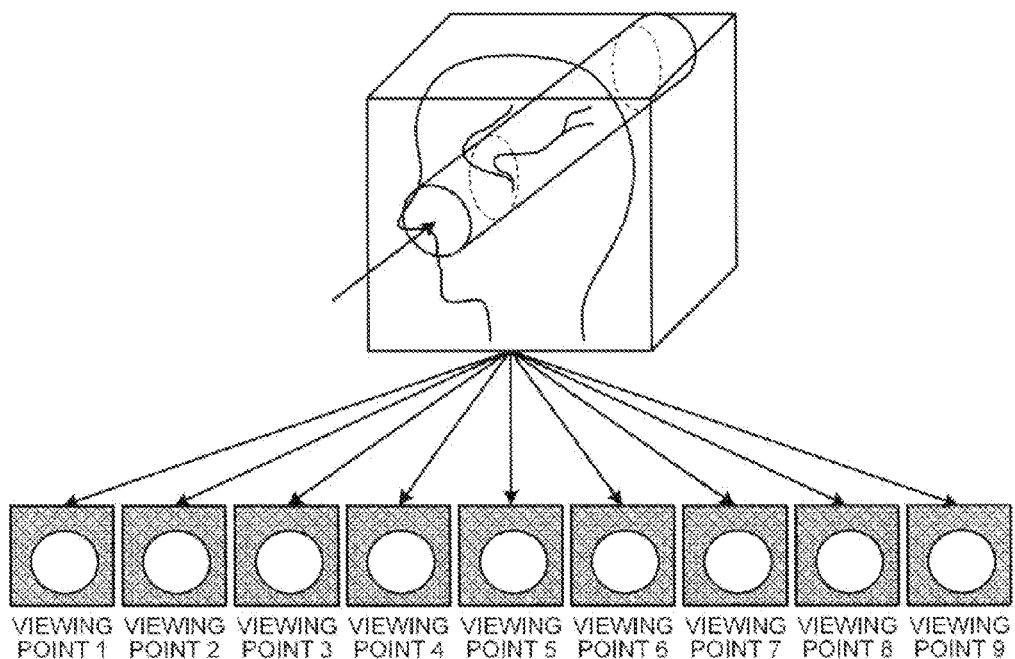
FIG. 12 is a view illustrating a stereoscopic image creating processing according to the first embodiment.

FIGS. 10 to 12 are views illustrating a stereoscopic image creating processing according to the first embodiment. In the first embodiment, the stereoscopic image is created, as illustrated in FIG. 10, by using the volume data of a cylindrical region that penetrates the entire volume data among the volume data. Further, FIG. 11 is a view that the volume data illustrated in FIG. 10 is observed from a parietal direction. As illustrated in FIG. 11, the stereoscopic image is created using the designated viewing point location as a "viewing point location 5" and "viewing point location 1" to "viewing point location 9" with a "viewing point location 5" in the middle of them as the rendering condition. For example, the stereoscopic image creating unit 135b, as illustrated in FIG. 12, uses the volume data in the cylindrical region to create the nine disparity images having a value "0" that is embedded in the background region. Further, in FIG. 12, the black portion has the value "0".

The planar image creating unit 135c creates the planar image. In the planar image, the same object as the object represented in the stereoscopic image is represented. Specifically, the planar image creating unit 135c uses the viewing point location and the stereoscopic region accepted from the stereoscopic region designation accepting unit 135a and the other rendering conditions to perform the volume rendering processing on the volume data read from the storage unit 134 by the rendering processing unit 136 to create an identical image group that is replaced by the disparity image group to be used. The planar image creating unit 135c transmits the created identical image group to the display controller 135d.

Figure 13:
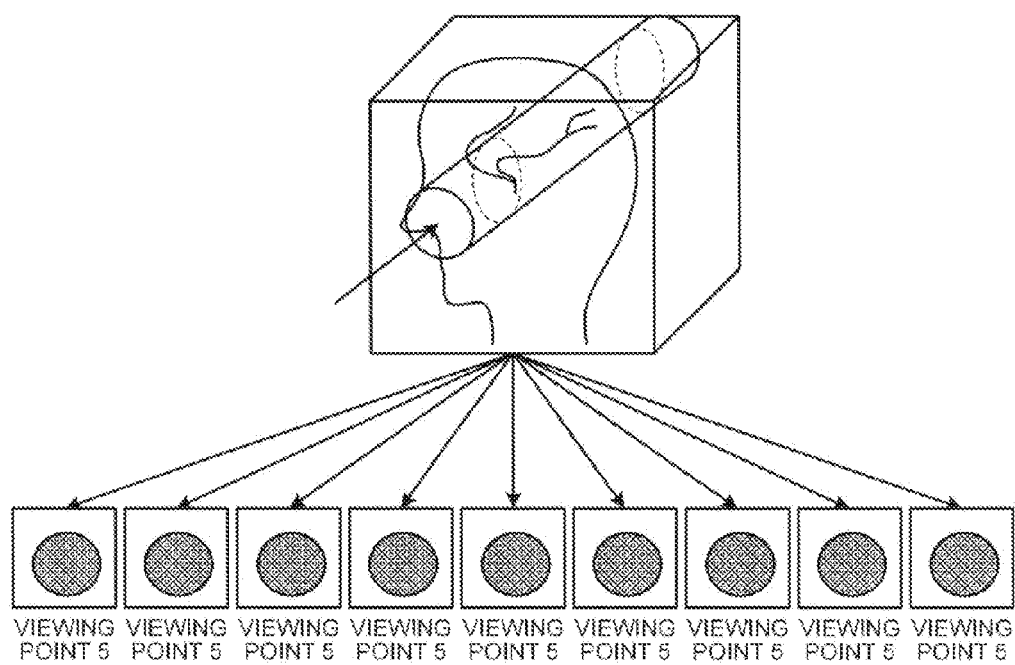
FIG. 13 is a view illustrating a planar image creating processing according to the first embodiment.

FIG. 13 is a view illustrating a planar image creating processing according to the first embodiment. In the first embodiment, the planar image is created using volume data other than the cylindrical region. The planar image is created using the "viewing point location 5" which is a designated viewing point location as the rendering condition. For example, the planar image creating unit 135c, as illustrated in FIG. 13, uses the volume data other than the cylindrical region to create the same disparity group having a value "0" that is embedded in the stereoscopic region. Further, in FIG. 13, the black portion has the value "0".

For example, the planar image creating unit 135c may extract one disparity image (for example, a disparity image corresponding to the "viewing point location 5") from the disparity image group created by the stereoscopic image creating unit 135b without performing the volume rendering processing again and copy the disparity image to create the identical image group.

The display controller 135d controls to superpose the stereoscopic image and the planar image and display the stereoscopic image and the planar image in the stereoscopic region and the background region, respectively. Specifically, the display controller 135d transforms the stereoscopic image accepted from the stereoscopic image creating unit 135b into an intermediate image to be displayed on the display unit 132 and uses the transformed intermediate image as an image of a layer 1. Further, the display controller 135d transforms the planar image accepted from the planar image creating unit 135c into an intermediate image to be displayed on the display unit 132 and uses the transformed intermediate image as an image of a layer 2. The display controller 135d superposes the image of the layer 1 and the image of the layer 2 to be displayed on the display unit 132. By doing this, the stereoscopic image is displayed in the stereoscopic region and the planar image is displayed in the background region.

Figure 14A:
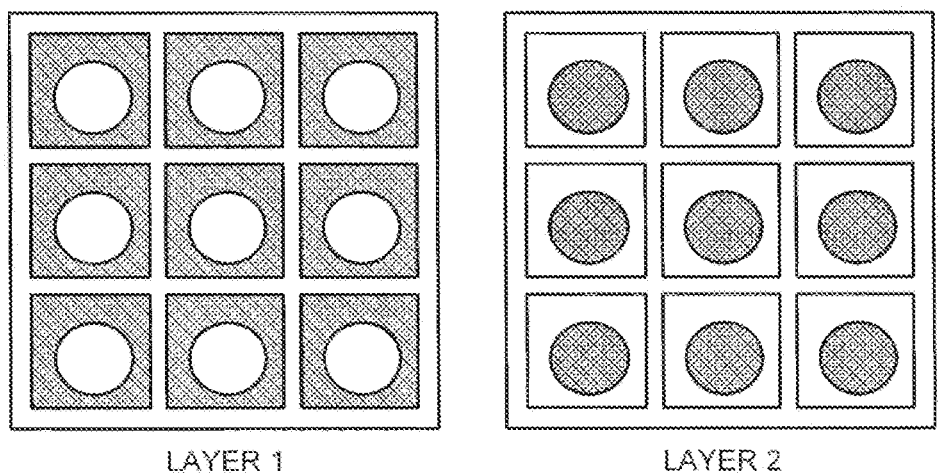
FIGS. 14A and 14B are views illustrating a display controlling processing according to the first embodiment.
Figure 14B:
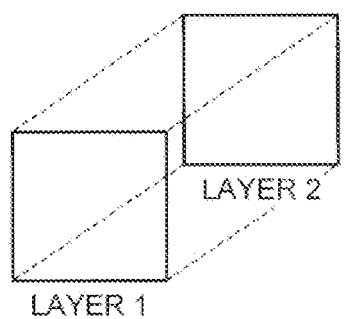

FIGS. 14A and 14B are views illustrating a display controlling processing according to the first embodiment. In the first embodiment, as illustrated in FIG. 14A, the intermediate image for displaying the stereoscopic image on the display unit 132 is an image in which the disparity image group illustrated in FIG. 12 and the identical image group illustrated in FIG. 13 are arranged in a lattice. The display controller 135d, as illustrated in FIG. 14B, superposes the layer 1 and the layer 2 to be displayed on the display unit 132.

The above-described the stereoscopic image creating processing, the planar image creating processing, and the display controlling processing are only examples. For example, the stereoscopic image creating unit 135b and the planar image creating unit 135c may perform the image creating processing using the entire volume data and the display controller 135d may perform, on the stereoscopic image, a mask processing for displaying only the stereoscopic region and on the planar image, a mask processing for displaying only the background region and then superpose both images. As described above, when the stereoscopic image and the planar image are created using the entire volume data, for example, the display controller 135d may accept the manipulation from the operator to switch to display the entire display surface with the stereoscopic image or to display the entire display surface with the planar image.

FIG. 15 is a flowchart illustrating procedures according to a first embodiment. As illustrated in FIG. 15, first, the stereoscopic region designation accepting unit 135a reads the volume data from the storage unit 134 (step S101), creates the image for designating from the read volume data and displays the created image for designating on the display unit 132 (step S102). Subsequently, the stereoscopic region designation accepting unit 135a accepts the designation of the viewing point location and the stereoscopic region on the image for designating (step S103).

The stereoscopic image creating unit 135b uses the viewing point location and the stereoscopic region accepted by the stereoscopic region designation accepting unit 135a to create the stereoscopic image (step S104). The planar image creating unit 135c uses the viewing point location and the stereoscopic region accepted by the stereoscopic region designation accepting unit 135a to create the planar image (step S105). The display controller 135d controls to display the stereoscopic image in the stereoscopic region and display the planar image in the background region (step S106).

However, the processing sequences illustrated in FIG. 15 are only examples. For example, the process of creating the stereoscopic image and the process of creating the planar image may be performed in a reverse order or simultaneously performed.

However, the work station 130 according to the first embodiment has the following additional functions to display the stereoscopic image and the planar image.

(Additional Function 1: Change of Viewing Position and Stereoscopic Region)

First, the work station 130 according to the first embodiment accepts the command for changing the viewing point location and the stereoscopic region on the display surface of the display unit 132 and updates the image which is being displayed in accordance with the accepted command for changing. Specifically, the stereoscopic region designation accepting unit 135a accepts the command for changing the viewing point location or the stereoscopic region on the display surface while the stereoscopic image and the planar image are displayed by the display controller 135d.

For example, the tool of the magnifier a may be enlarged or reduced and moved on the display surface of the display unit 132 in response to the operation of a mouse which is the input unit 131. Further, the object that is represented in the stereoscopic image and the planar image is rotatable in the display surface in response to the manipulation of the mouse. Therefore, for example, the stereoscopic region designation accepting unit 135a accepts the circular region indicated by the magnifier a that was manipulated by the mouse, as the changed stereoscopic region. Further, the stereoscopic region designation accepting unit 135a accepts a direction perpendicular to the image, which is displayed on the display surface when the designation of the changed stereoscopic region is accepted, as the changed viewing point location.

By doing this, the stereoscopic image creating unit 135b and the planar image creating unit 135c use the changed viewing point location and stereoscopic region and the other rendering conditions to perform the volume rendering processing on the volume data read from the storage unit 134 by the rendering processing unit 136 again to create a new stereoscopic image or planar image. Therefore, the display controller 135d controls to superpose the newly created stereoscopic image and planar image and display the newly created stereoscopic image and planar image in the changed stereoscopic region and the changed background region, respectively.

As described above, when the stereoscopic image or the planar image is created using the entire volume data but the viewing point location is not changed, for example, the display controller 135d may update the screen which is being displayed by only changing the location of the mask processing without newly creating the stereoscopic image or the planar image.

(Additional Function 2: Change of Stereoscopic Effect)

Next, the work station 130 according to the first embodiment accepts the command for changing the stereoscopic effect of the stereoscopic image in the stereoscopic region and updates the image which is being displayed in accordance with the accepted command for changing. Specifically, the stereoscopic region designation accepting unit 135a accepts the command for changing the stereoscopic effect by, for example, manipulating a tool bar displayed on the display surface using the mouse while the stereoscopic image and the planar image are displayed by the display controller 135d.

Here, the stereoscopic effect of the stereoscopic image is determined by the disparity angle. For example, comparing the case when a disparity angle "0.5 degree" is designated and the case when a disparity angle "1 degree" is designated, when the disparity angle "1 degree" is designated, the stereoscopic effect is larger. For example, it is known that the stereoscopic image creating unit 135b uses the disparity angle "0.5 degree" set as an initial value to create the stereoscopic image. Thereafter, it is known that the command for changing so as to increase the stereoscopic effect is accepted and "1 degree" is designated as the disparity angle. By doing this, the stereoscopic image creating unit 135b performs the volume rendering processing on the volume data read from the storage unit 134 by the rendering processing unit 136 again using the changed disparity angle "1 degree" as a new rendering condition to create a new stereoscopic image. The display controller 135d replaces the stereoscopic image to be displayed as an image of the layer 1 with a newly created stereoscopic image.

(Additional Function 3: Change of Enlargement/Reduction Ratio)

Next, the work station 130 according to the first embodiment accepts the command for changing the enlargement ratio or the reduction ratio (hereinafter, enlargement/reduction ratio) of the stereoscopic image in the stereoscopic region and updates the image which is being displayed in accordance with the accepted command for changing. Specifically, the stereoscopic region designation accepting unit 135a accepts the command for changing the enlargement/reduction ratio by manipulating a tool bar displayed on the display surface using the mouse while the stereoscopic image and the planar image are displayed by the display controller 135d.

For example, it is known that the stereoscopic image creating unit 135b uses the enlargement/reduction ratio "100%" set as an initial value to create the stereoscopic image. Thereafter, the command for changing the enlargement direction is accepted and "115%" is designated as the enlargement/reduction ratio. By doing this, the stereoscopic image creating unit 135b performs the volume rendering processing on the volume data read from the storage unit 134 by the rendering processing unit 136 again using the changed enlargement/reduction ratio "115%" as a new rendering condition to create a new stereoscopic image. The display controller 135d replaces the stereoscopic image to be displayed as an image of the layer 1 with a newly created stereoscopic image.

Modification Example of the First Embodiment

So far, the display examples and the additional functions according to the first embodiment are described, but the embodiment is not limited thereto.

In the above-described display examples, the "stereoscopic image" is displayed in the designated region and the "planar image" is displayed in the background region. Further, the "planar image" uses one disparity image among the disparity image group for displaying the stereoscopic image as the same image which is replaced with the disparity image group.

In other words, the "stereoscopic image" is an image created by performing the volume rendering processing on the volume data and three-dimensionally displayed on the stereoscopic display monitor. In the meantime, the "planar image" is an image created by performing the volume rendering processing on the volume data, but two-dimensionally displayed on the stereoscopic display monitor. That is, the above-described display examples three-dimensionally display the volume rendering image in the designated region and two-dimensionally display the volume rendering image in the background region.

However, the embodiment is not limited thereto. For example, the volume rendering image may be two-dimensionally displayed in the designated region and the volume rendering image may be three-dimensionally displayed in the background region. The two-dimensionally displayed "planar image" is not limited to the "volume rendering image". For example, the two-dimensionally displayed "planar image" may be a "surface rendering image", an "MPR image", an "MIP (maximum intensity projection) image", or an "MinIP (minimum intensity projection) image". The MIP image refers to a maximum intensity projection image and the MinIP image refers to a minimum intensity projection image. In this case, the object that is represented in the planar image does not necessarily match with the object that is represented in the stereoscopic image, but the objects may correspond to each other. That is, for example, when a brain blood vessel of the object is represented in the stereoscopic image, the object which is represented in the planar image is also the same brain blood vessel of the same object, but the image on which the same rendering processing is performed is not a two-dimensionally displayed image, but an image on which different rendering processing is performed.

Figure 16A:
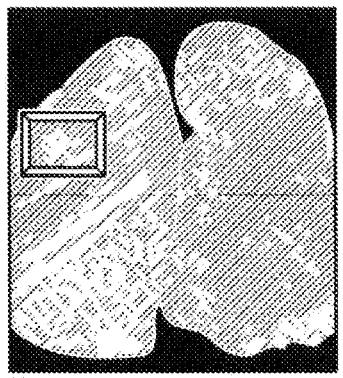
FIGS. 16A to 16C are views illustrating a modification example of the first embodiment.
Figure 16B:
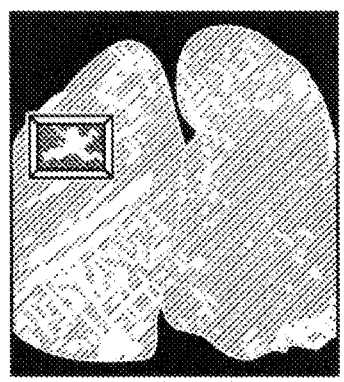
Figure 16C:
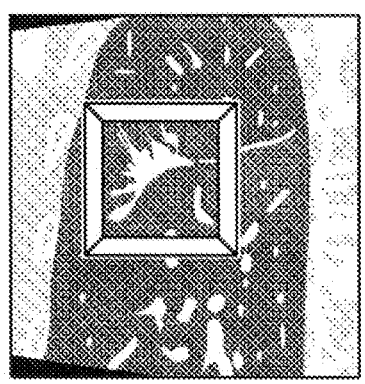

Further, the "stereoscopic image" may be, for example, an image that is deformed like an icon that is represented by a stereoscopically viewable figure (hereinafter, icon stereoscopic image). FIGS. 16A to 16C are views illustrating a modification example of the first embodiment. For example, referring to FIG. 16A, the "volume rendering image" is two-dimensionally displayed in the background region and the "icon stereoscopic image" is three-dimensionally displayed in the designated region. Further, the "volume rendering image" is attached onto the surface of the "icon stereoscopic image" as the "planar image".

For example, referring to FIG. 16B, the "volume rendering image" is two-dimensionally displayed in the background region and the "icon stereoscopic image" is three-dimensionally displayed in the designated region. Further, the "MPR image" is attached onto the surface of the "icon stereoscopic image". For example, referring to FIG. 16C, the "MPR image" is two-dimensionally displayed in the background region and the "icon stereoscopic image" is three-dimensionally displayed in the designated region. Further, the "MPR image" is attached onto the surface of the "icon stereoscopic image".

A method of displaying the "icon stereoscopic image" in the designated region will be described. For example, the storage unit 134 stores cubical, rectangular, or cylindrical volume data having various sizes as the volume data for icon separately from the volume data as medical image data. For example, the stereoscopic image creating unit 135b creates a disparity image group to be attached on the surface of the "icon stereoscopic image" from the volume data as the medical image data read from the storage unit 134 and a display image group for displaying the main body of the "icon stereoscopic image" from the volume data for icon read from the storage unit 134. The stereoscopic image creating unit 135b superposes the disparity image group for displaying the main body of the "icon stereoscopic image" with the disparity image group to be attached onto the surface of the "icon stereoscopic image" to create the disparity image group for displaying the "icon stereoscopic image". The storage unit 134 may store, in advance, the disparity image group for displaying the main body of the "icon stereoscopic image" corresponding to the various sizes.

As described above, the combination of the stereoscopic image and the planar image may be appropriately modified in accordance with the operational forms. Some of them will be described in the following table 1. In table 1, an image which is attached onto the icon stereoscopic image is disclosed in the brackets.

TABLE 1

| Designated region | Background region |
|---|---|
| Stereoscopic image | Volume rendering image (Two-dimensional display) |
| Volume rendering image (Two-dimensional display) | Stereoscopic image |
| Stereoscopic image | MPR image |
| MPR image (Two-dimensional display) | Stereoscopic image |
| Stereoscopic image | MIP image |
| MIP image (Two-dimensional display) | Stereoscopic image |
| Icon stereoscopic image (Volume rendering image) | Volume rendering image (Two-dimensional display) |
| Icon stereoscopic image (MPR image) | Volume rendering image (Two-dimensional display) |
| Icon stereoscopic image (MIP image) | Volume rendering image |
| Icon stereoscopic image (Volume rendering image) | MPR image |
| Icon stereoscopic image (MPR image) | MPR image |
| Icon stereoscopic image (MIP image) | MPR image |
| Icon stereoscopic image (Volume rendering image) | MIP image |
| Icon stereoscopic image (MPR image) | MIP image |
| Icon stereoscopic image (MIP image) | MIP image |

Further, a "surface rendering image" may be used instead of the "volume rendering image" in Table 1. Further, the "MinIP image" may be used instead of the "MIP image". In the above description, it is mainly described that the stereoscopic image is viewed as a sense of protruding from the display surface to the front. However, the embodiments are not limited thereto, but may be applied when the stereoscopic image is viewed as a sense of depth from the display surface to the depth direction or when both the sense of protruding and the sense of depth are viewed. For example, if the object that is represented in the stereoscopic image is a lung field, the lung field may be divided into a front side and a rear side from the center thereof. And then, the stereoscopic image and the planar image may be created and displayed so as to view the front side as a sense of protrusion and the rear side as a sense of depth. By doing this, the observer who watches the stereoscopic image and the planar image may easily interpret the images. Further, the sense of protrusion and the sense of depth may be set in advance as, for example, one of rendering conditions.

Further, the additional functions may be applied to the above modification example. That is, the viewing point location, the change of the designated region, the change of the stereoscopic effect, and the change of the enlargement/reduction ratio may be also similarly applied to the above modification example.

Effect of First Embodiment

As described above, according to the first embodiment, since the stereoscopic image and the planar image are displayed in the designated region and the background region in the display surface, respectively, as compared with the method that the stereoscopic image is displayed on the entire region of the display surface, the stress may be reduced, a desired region may be focused, and the medical image may be appropriately displayed.

Second Embodiment

Next, a second embodiment will be described. As described as the modification example of the first embodiment, the embodiment includes an example that three-dimensionally displays the "stereoscopic image" in the designated region and two-dimensionally displays the "MPR image" in the background region, an example that two-dimensionally displays the "MPR image" in the designated region and three-dimensionally displays the "stereoscopic image" in the background region, or an example that three-dimensionally displays the "icon stereoscopic image" to which the "MPR image" is attached in the designated region and two-dimensionally displays the "volume rendering image" in the background region. Here, a work station 130 according to the second embodiment accepts the designation of a cross-section position of the "MPR image" that is two-dimensionally displayed in the designated region or the background region and updates the image which is being displayed in accordance with the accepted designation of the cross-section position. Also, in the second embodiment, it is mainly described that the stereoscopic image is viewed as a sense of protruding from the display surface to the front. However, the embodiment is not limited thereto, but may be similarly applied when the stereoscopic image is viewed as a sense of depth from the display surface to the depth direction or when both the sense of protrusion and the sense of depth are viewed.

Figure 17:
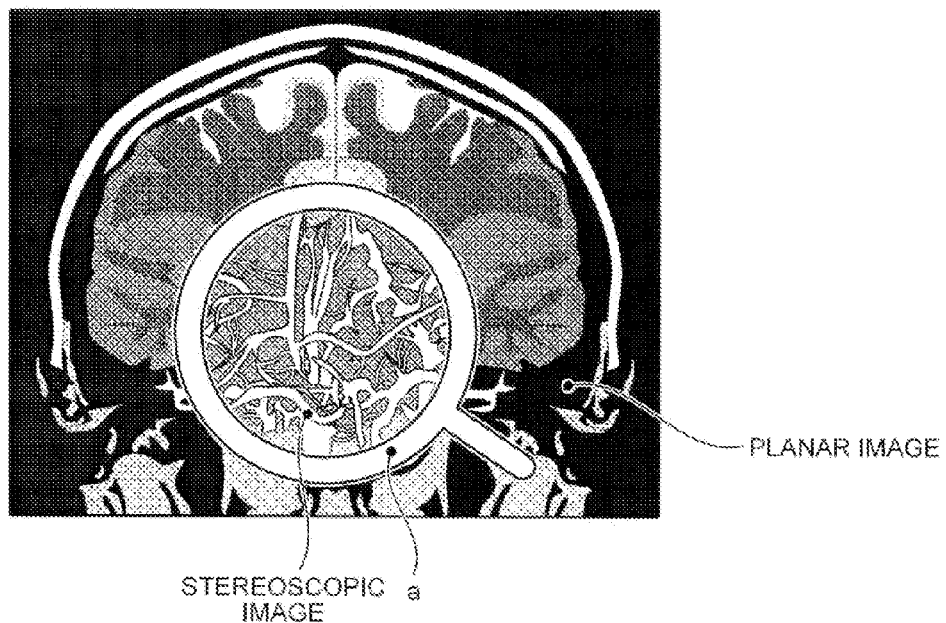
FIG. 17 is a view illustrating a display example according to a second embodiment.
Figure 18:
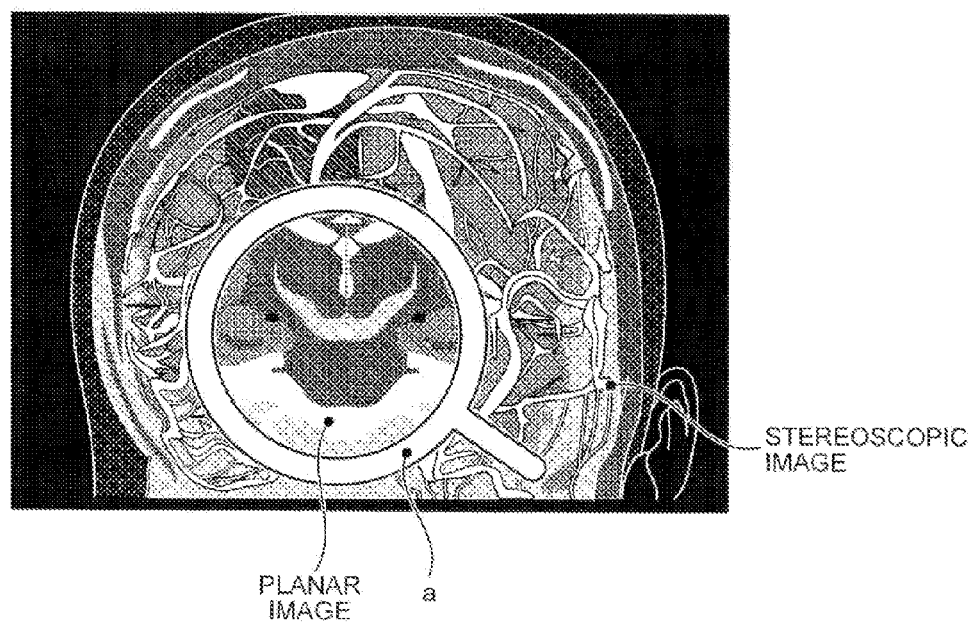
FIG. 18 is a view illustrating a display example according to the second embodiment.

FIGS. 17 to 19B are views illustrating a display example according to the second embodiment. As illustrated in FIG. 17, the work station 130 according to the second embodiment three-dimensionally displays the stereoscopic image in the designated region and two-dimensionally displays the MPR image in the background region. Alternatively, as illustrated in FIG. 18, the work station 130 according to the second embodiment two-dimensionally displays the MPR image in the designated region and three-dimensionally displays the stereoscopic image in the background region. Alternatively, as illustrated in FIG. 19A, the work station 130 according to the second embodiment three-dimensionally displays the icon stereoscopic image in the designated region and two-dimensionally displays the volume rendering image in the background region. Further, the MPR image is attached onto the surface of the icon stereoscopic image.

Figure 20:
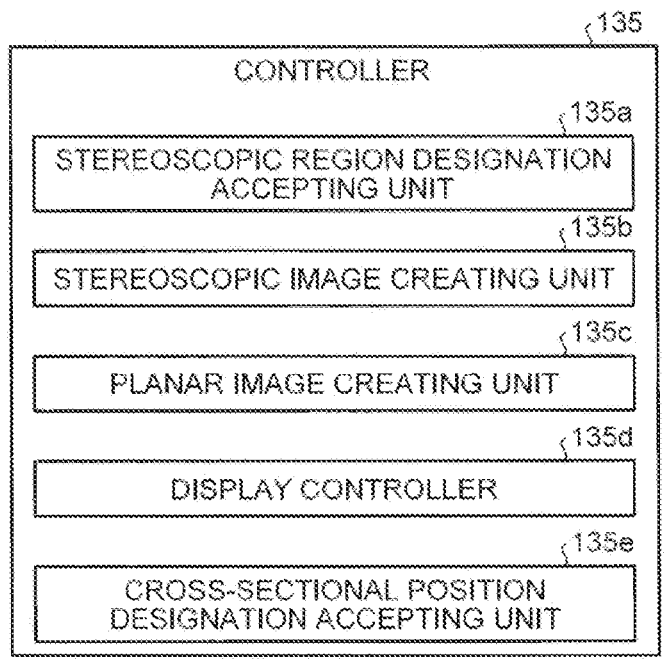
FIG. 20 is a view illustrating a configuration example of a controller according to the second embodiment.

FIG. 20 is a view illustrating a configuration example of a controller 135 according to the second embodiment. As illustrated in FIG. 20, the controller 135 according to the second embodiment further includes a cross-sectional position designation accepting unit 135e. The cross-sectional position designation accepting unit 135e accepts the designation of the cross-sectional position from the operator through an input unit 131 and transmits the accepted designation of the cross-sectional position to a stereoscopic image creating unit 135b or a planar image creating unit 135c. For example, the cross-sectional position designation accepting unit 135e accepts the designation of the cross-sectional position by manipulating a tool bar displayed on the display surface using the mouse while the stereoscopic image and the planar image are displayed by a display controller 135d.

Figure 19A:
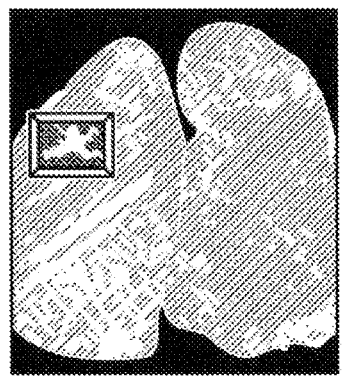
FIGS. 19A and 19B are views illustrating a display example according to the second embodiment.
Figure 19B:
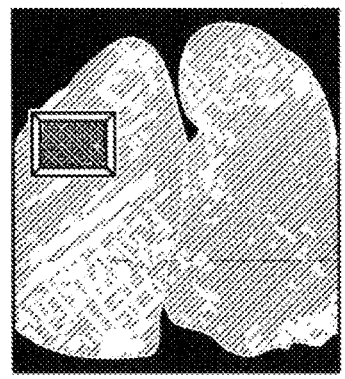

By doing this, the stereoscopic image creating unit 135b or the planar image creating unit 135c performs the volume rendering processing on the volume data read from a storage unit 134 by the rendering processing unit 136 again using the designated cross-sectional position as a new rendering condition to create a new MPR image. The display controller 135 replaces the MPR image to be displayed as an image of the layer 1 or the layer 2 with a newly created MPR image. For example, FIG. 19B illustrates an example that the MPR image attached onto the surface of the icon stereoscopic image is replaced with the newly created MPR image.

Effect of Second Embodiment

As described above, according to the second embodiment, designation of the cross-section position of the MPR image that is two-dimensionally displayed in the designated region or the background region is accepted and the image which is being displayed is updated in accordance with the accepted designation of the cross-section position. Therefore, the operator may browse while changing the cross-sectional position.

Third Embodiment

Next, a third embodiment will be described. A work station 130 according to the third embodiment does not accept the designation of the designated region from the operator, but specifies the designated region based on an analysis result of the medical image data.

Figure 21:
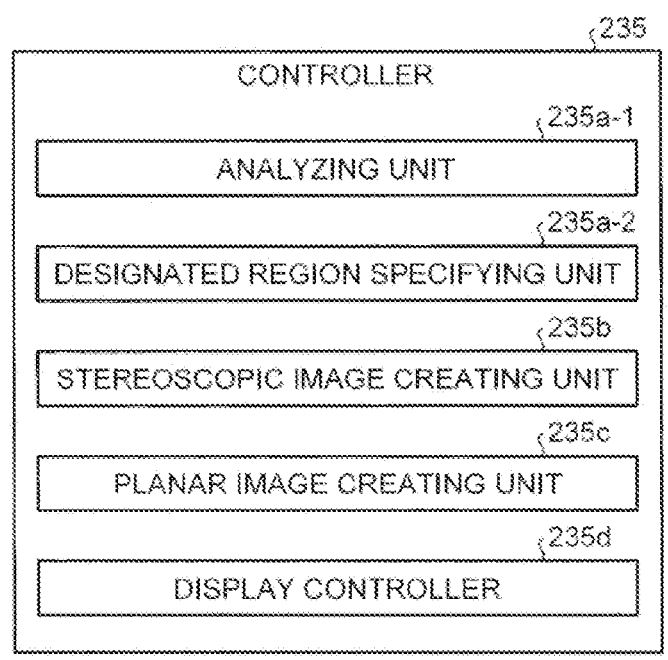
FIG. 21 is a view illustrating a configuration example of a controller according to a third embodiment.

The work station 130 according to the third embodiment includes a controller 235 instead of the controller 135. FIG. 21 is a view illustrating a configuration example of the controller 235 according to the third embodiment. As illustrated in FIG. 21, the controller 235 according to the third embodiment includes an analyzing unit 235a-1 and a designated region specifying unit 235a-2 instead of the stereoscopic region designation accepting unit 135a. Further, since a stereoscopic image creating unit 235b, a planar image creating unit 235c, and a display controller 235d have functions corresponding to the stereoscopic image creating unit 135b, the planar image creating unit 135c, and the display controller 135d, the description those of will be omitted.

The analyzing unit 235a-1 analyzes the medical image data such as the volume data and outputs the analysis result. For example, the analyzing unit 235a-1 reads the volume data from the storage unit 134 and analyzes the read volume data in accordance with the predetermined analyzing algorithm to output the analysis result. The analyzing unit 235a-1 transmits the output analysis result to the designated region specifying unit 235a-2.

Here, the analysis by the analyzing unit 235a-1 may be embodied by, for example, an existing automatic diagnosis technology (CAD: computer aided diagnosis). For example, the analyzing unit 235a-1 judges each of the regions included in the object by a plurality of judgment items set in advance, and if at least one item of the plurality of judgment items exceeds a threshold, outputs an analysis result indicating the position of the corresponding region. For example, the judgment items include a size of a region which is suspected as a tumor, a shape of the region which is suspected as a tumor, a location of the region which is suspected as a tumor, a spicula degree of a blood vessel, a spicula degree of bronchial tube, or existence of contrast.

The designated region specifying unit 235a-2 specifies the designated region based on the analysis result by the analyzing unit 235a-1. For example, if the position of the "region which is suspected as a tumor" is accepted as the analysis result from the analyzing unit 235a-1, the designated region specifying unit 235a-2 specifies the predetermined range of the region including the "region which is suspected as a tumor" as the designated region. Therefore, the designated region specifying unit 235a-2 transmits the specified designated region to the stereoscopic image creating unit 235b, and the planar image creating unit 235c. In the third embodiment, the viewing point location may use a predetermined initial value or the designation thereof may be accepted similarly to the first or second embodiment.

FIG. 22 is a flowchart illustrating procedures according to the third embodiment. As illustrated in FIG. 22, first, the analyzing unit 235a-1 analyzes the volume data read from a storage unit 134 in accordance with a predetermined analyzing algorithm and outputs the position of a region which is suspicious of abnormality as an analysis result (step S201).

Subsequently, the designated region specifying unit 235a-2 specifies the predetermined range of region including the position accepted from the analyzing unit 235a-1 as the designated region (step S202).

Thereafter, similarly to the first and second embodiments, the stereoscopic image creating unit 235b creates the stereoscopic image (step S203), the planar image creating unit 235c creates the planar image (step S204), the display controller 235d controls to, for example, three-dimensionally display the stereoscopic image in the designated region and two-dimensionally display the planar image in the background region (step S205). Also, in the third embodiment, the planar image may be two-dimensionally displayed in the designated region and the stereoscopic image may be three-dimensionally displayed in the background region. Further, the combination of the stereoscopic image and the planar image may be appropriately modified in accordance with the operational forms.

Modification Example 1 of Third Embodiment

As the third embodiment, an example that the analysis by the analyzing unit 235a-1 is embodied by the existing automatic diagnostic technology is described. However, the embodiment is not limited thereto.

For example, the analysis by the analyzing unit 235a-1 may be embodied by an existing CBP (cerebral blood perfusion) technology. For example, the analyzing unit 235a-1 analyzes medical image data collected by continuous rapid scanning while administrating a contrast agent and outputs the amount of blood per unit time (hereinafter, referred to as MAP value) as the analysis result. When the MAP value is accepted from the analyzing unit 235a-1, the designated region specifying unit 235a-2 specifies the region, in which the MAP value exceeds a predetermined threshold, as the designated region. Therefore, the designated region specifying unit 235a-2 transmits the specified designated region to the stereoscopic image creating unit 235b, and the planar image creating unit 235c.

By doing this, the stereoscopic image creating unit 235b creates a usual MAP image and creates the disparity image group so as to stereoscopically view only the designated region of the created MAP image. Even though any methods may be used to create the image, for example, the stereoscopic image creating unit 135b may use the same method as the method of creating the above-described "icon stereoscopic image".

In other words, for example, the stereoscopic image creating unit 235b creates the disparity image group for displaying on a cylindrical surface corresponding to a circle of the designated region from the normal MAP image and creates the disparity image group for displaying a cylindrical main body from the icon volume data. The stereoscopic image creating unit 235b superposes the disparity image group for displaying the cylindrical main body with the disparity image group for displaying on the cylindrical surface. In the meantime, the planar image creating unit 235c creates the identical image group for displaying the normal MAP image as the planar image.

FIGS. 23A and 23B are views illustrating a display example according to a modification example of the third embodiment. FIG. 23A is an MAP image that does not include a stereoscopic image and FIG. 23B is an MAP image that displays a region, where the MAP value exceeds a predetermined threshold, as a stereoscopically viewable cylinder. Usually, the region where the MAP value exceeds the predetermined threshold is a lesion portion. According to the third embodiment, as illustrated in FIG. 23B, since the lesion portion is stereoscopically displayed, it is possible to reduce a failure to catch the lesion portion.

Modification Example 2 of Third Embodiment

Next, in the first or second embodiments, a method of displaying the "MPR image" in the designated region or the background region has been described. In the third embodiment, a method of specifying the stereoscopic region based on the analysis result of the medical image data without accepting the designation of the stereoscopic region from the operator has been described. Here, in the modification example 2, a method of specifying a cross-sectional location of the "MPR image" to be displayed in the designated region or the background region based on the analysis result of the medical image data will be described.

That is, as described above, if the analysis by the analyzing unit 235a-1 is achieved by, for example, the existing automatic diagnostic technology, the analyzing unit 235a-1 may output the location of a region that is specious of abnormality as the analysis result. The designated region specifying unit 235a-2, as described above, specifies a predetermined range of region including the location as the designated region, and specifies the cross-sectional location of the "MPR image" based on the location. For example, the designated region specifying unit 235a-2 calculates a center of the region which is specious of abnormality and specifies the location of the calculated center as the cross-sectional location of the "MPR image". The designated region specifying unit 235a-2 transmits information of the cross-sectional location to the stereoscopic image creating unit 235b or the planar image creating unit 235c and the stereoscopic image creating unit 235b and the planar image creating unit 235c create the MPR image using the specified cross-sectional location as the rendering condition.

Effect of Third Embodiment

As described above, according to the third embodiment, the designated region may be automatically specified based on the analysis result by the existing automatic diagnostic technology or an existing CBP technology. Therefore, it is possible to more appropriately display the analysis result.

Further, for example, when lung cancer screening using an X-ray CT device is introduced, it is considered that the amount of images which are targets of interpretation will be significantly increased. Further, the automatic diagnostic technology is already used for breast cancer or colorectal cancer. Therefore, according to the third embodiment, it is possible to efficiently support the interpretation.

Fourth Embodiment

Next, a fourth embodiment will be described. A work station 130 according to the fourth embodiment uses an assumption that the designated region is specified based on the analysis result of the medical image data, similarly to the third embodiment. Further, the work station 130 specifies the stereoscopic effect of the stereoscopic image based on the analysis result.

For example, when an analysis by the analyzing unit 235a-1 is achieved by the existing automatic diagnostic technology, a designated region specifying unit 235a-2 accepts the number of judgment items that exceed the threshold as the analysis result and specifies the stereoscopic effect in accordance with the number of judgment items. For example, when the predetermined judgment items are 10 items, the designated region specifying unit 235a-2 specifies one tenth stereoscopic effect of maximum stereoscopic effect as one unit of stereoscopic effect. Further, if the number of judgment items that exceed the threshold is "2", the designated region specifying unit 235a-2 specifies the stereoscopic effect as "2". The designated region specifying unit 235a-2 transmits the stereoscopic effect "2" to a stereoscopic image creating unit 235b.

By doing this, the stereoscopic image creating unit 235b performs the volume rendering processing on the volume data read from a storage unit 134 by a rendering processing unit 136 using the disparity angle corresponding to the stereoscopic effect "2" as a rendering condition to create the disparity image group. The display controller 235d three-dimensionally displays the disparity image group.

For example, when the analysis by the analyzing unit 235a-1 is achieved by the existing CBP technology, the designated region specifying unit 235a-2 accepts the MAP value as the analysis result and specifies the stereoscopic effect in accordance with the MAP value. The designated region specifying unit 235a-2 transmits the specified stereoscopic effect to the stereoscopic image creating unit 235b. By doing this, the stereoscopic image creating unit 235b performs the volume rendering processing on the volume data read from the storage unit 134 by the rendering processing unit 136 using the disparity angle corresponding to the stereoscopic effect as a rendering condition to create the disparity image group. The display controller 235d three-dimensionally displays the disparity image group.

(Stereoscopic Effect of Icon Stereoscopic Image)

Figure 24:
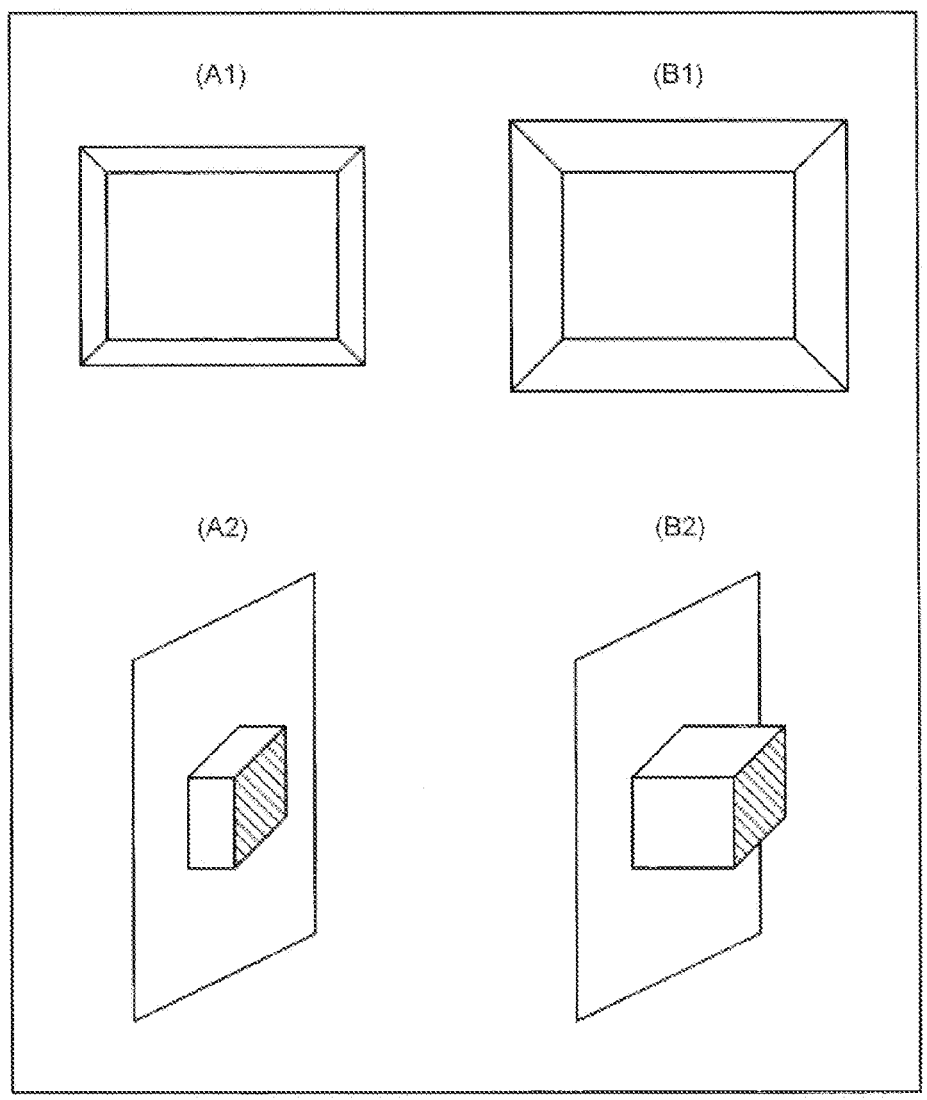
FIG. 24 is a view illustrating an icon stereoscopic image according to a fourth embodiment.

However, the stereoscopic effect is effectively specified based on the analysis result using the "icon stereoscopic image" as the stereoscopic image. FIG. 24 is a view illustrating an icon stereoscopic image according to the fourth embodiment. As it is apparent when (A1) of FIG. 24 is compared with (A2) of FIG. 24 and (B1) of FIG. 24 is compared with (B2) of FIG. 24, if the "icon stereoscopic image" is used as the stereoscopic image, the stereoscopic effect corresponds to the height of the icon. Therefore, the observer may easily catch the difference of the stereoscopic effect. Further, (A2) and (B2) of FIG. 24 are views when the icons of (A1) and (B1) of FIG. 24 are observed from the side.

When the analysis by the analyzing unit 235a-1 is achieved by the existing automatic diagnostic technology, as described above, the designated region specifying unit 235a-2 accepts the number of judgment items that exceed the threshold as the analysis result and specifies the stereoscopic effect in accordance with the number of judgment items. For example, if the number of judgment items that exceed the threshold is "2", the designated region specifying unit 235a-2 specifies that the stereoscopic effect is "2". The designated region specifying unit 235a-2 transmits the stereoscopic effect "2" to the stereoscopic image creating unit 235b.

By doing this, the stereoscopic image creating unit 235b selects volume data for icon corresponding to the stereoscopic effect "2" from the volume data for icon and creates the disparity image group for displaying the "icon stereoscopic image" using the selected volume data. It may also be similarly achieved when the analysis by the analyzing unit 235a-1 is achieved by the existing CBP technology.

Further, when the "icon stereoscopic image" is used as the stereoscopic image, the analysis result may be reflected to a color of the "icon stereoscopic image". For example, the designated region specifying unit 235a-2 determines that the degree that is suspicious of abnormality is "low level" from the number of judgment items that exceed the threshold and notifies the stereoscopic image creating unit 235b of that fact. The stereoscopic image creating unit 235b colors a color of the "icon stereoscopic image" which is a color around a cubic, a rectangular, and a cylinder with a color corresponding to the "low level" (for example, blue) to display the "icon stereoscopic image". For example, an "intermediate level" may be colored with yellow and a "high level" may be colored with red.

When, for example, a degree of malignancy of a tumor is output as the analysis result by the analyzing unit 235a-1, the designated region specifying unit 235a-2 may specify the stereoscopic effect not only in accordance with the number of judgment items or the MAP value but also in accordance with the degree of malignancy.

Modification Example of Fourth Embodiment

In addition to the method of specifying the stereoscopic effect of the stereoscopic image based on the analysis result, for example, the stereoscopic effect of the stereoscopic image may be specified using the relationship of the cross-sectional location of the "MPR image" that is two-dimensionally displayed in the designated region or the background region.

Figure 25A:
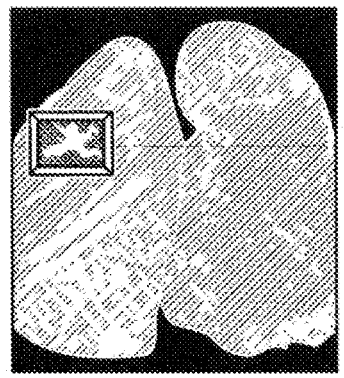
FIGS. 25A and 25B are views illustrating a display example according to a modification example of the fourth embodiment.
Figure 25B:
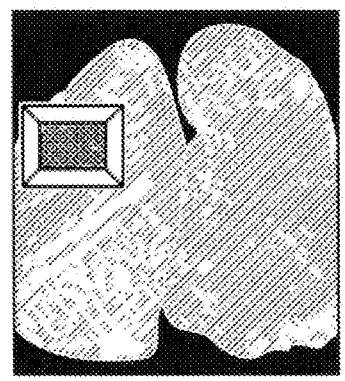

FIGS. 25A and 25B are views illustrating a display example according to a modification example of the fourth embodiment. As illustrated in FIGS. 25A and 25B, for example, when the "volume rendering image" is two-dimensionally displayed in the background region, the "icon stereoscopic image" is three-dimensionally displayed in the designated region, and the "MPR image" is attached on the surface of the "icon stereoscopic image", the stereoscopic image creating unit 235b changes the height of the "icon stereoscopic image" in accordance with the cross-sectional location of the "MPR image".

That is, the designated region specifying unit 235a-2 specifies the coordinate (coordinate of a depth direction) on the three-dimensional space for the cross-sectional location displayed as the "MPR image". Therefore, the stereoscopic image creating unit 235b selects volume data for icon corresponding to the coordinate of the depth direction from the volume data for icon and creates the disparity image group for three-dimensionally displaying the "icon stereoscopic image" using the selected volume data.

For example, as known when a height of the "icon stereoscopic image" illustrated in FIG. 25A is compared with a height of the "icon stereoscopic image" illustrated in FIG. 25B, the "icon stereoscopic image" illustrated in FIG. 25B is higher than the "icon stereoscopic image" illustrated in FIG. 25A. This indicates that the cross-sectional location of the "MPR image" attached on the "icon stereoscopic image" illustrated in FIG. 25B is more forward than the cross-sectional location of the "MPR image" attached on the "icon stereoscopic image" illustrated in FIG. 25A.

As described above, in the fourth embodiment, the stereoscopic effect may be specified based on the analysis result or specified by the relationship with the cross-sectional location of the "MPR image". For example, the work station 130 may switch both functions.

Effect of Fourth Embodiment

As described above, according to the fourth embodiment, the stereoscopic effect of the stereoscopic image may be adjusted based on the analysis result by the existing automatic diagnostic technology or an existing CBP technology. Therefore, it is possible to more appropriately display the analysis result.

Other Embodiments

Other embodiments will be described.
(Display of 4D Data)
In the above-described embodiments, a method of displaying the stereoscopic image and the planar image in the designated region and the background region in the display surface, respectively, is described. However, as one or both the stereoscopic image and the planar image, 4D data may be used. That is, the stereoscopic image and the planar image may be continuously reproduced in time series manner.

In this case, the movement due to the time transition may be tracked and the designated region may be moved in conjugation with the tracking result. For example, it is effective when the location of the tumor is moved due to the action of breathing. The designated region specifying unit 235a-2 specifies an initial designated region based on the analysis result, and then tracks the movement of the image (for example, tumor) included in the designated region due to the time transition and changes the designated region in conjugation with the tracking result to notify the display controller 235d. By doing this, the display controller 235d changes, for example, the location of masking processing to move the designated region.

Alternatively, the display controller 235d may change the background image without moving the designated region. In this case, for example, the designated region specifying unit 235a-2 notifies the tracking result to the stereoscopic image creating unit 235b or the planar image creating unit 235c that create the background image. The stereoscopic image creating unit 235b or the planar image creating unit 235c creates the stereoscopic image or the planar image of which the location is moved in accordance with the tracking result.
(Diagnostic Report)

Figure 26:
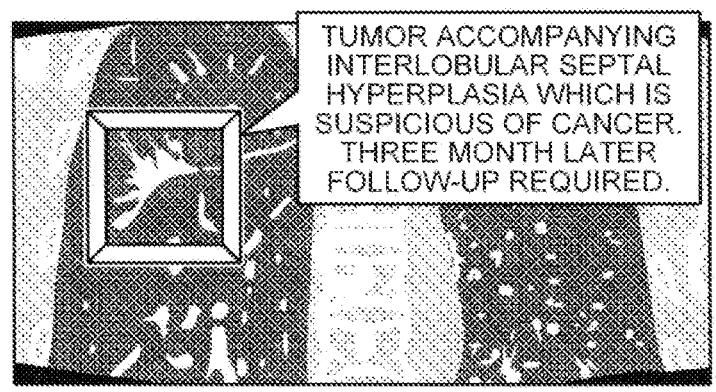
FIG. 26 is a view illustrating a display example according to other embodiment.

Further, the diagnostic report may be automatically created based on the image displayed in the above-described embodiment. FIG. 26 is a view illustrating a display example according to the other embodiments. For example, when the image illustrated in FIG. 26 is displayed, the operator such as a doctor may add a comment onto the image. The operator such as a doctor may manipulate the input unit 131 (for example, manipulates a wheel of a mouse which is the input unit 131) to change the stereoscopic effect of the "icon stereoscopic image". For example, if the operator such as a doctor browses the image and then diagnoses that "it is not a cancer", the operator sets the height of the "icon stereoscopic image" to "0". The work station 130 stores the image with the comment added thereto and the adjusted height of the "icon stereoscopic image" in the storage unit 134 as the diagnostic report.

For example, if the operator such as a doctor browses the image and then diagnoses that "it is considered to be positive but suspiciousness remains", the operator manipulates the input unit 131, and changes the stereoscopic effect of the "icon stereoscopic image" so that the height is a little bit small, for example, while remaining the stereoscopic effect of the "icon stereoscopic image". The operator such as a doctor may manipulate the input unit 131 to change the height of the "icon stereoscopic image" in accordance with the diagnostic content (for example, the degree of malignancy of cancer). In other words, the work station 130 according to the fourth embodiment accepts the change of the stereoscopic effect of the "icon stereoscopic image", creates a new stereoscopic image in accordance with the accepted stereoscopic effect, and stores the stereoscopic image in the storage unit 134 as the diagnostic report, through the manipulation of the input unit 131 by the operator.
(Configuration)

Further, in the above-described embodiments, it has been described that the work station 130 creates the stereoscopic image and the planar image and controls the display thereof. However, the embodiments are not limited thereto. For example, the medical image diagnostic apparatus 110 and the terminal device 140 may have a function corresponding to the controller 135 or the rendering processing unit 136 or a function corresponding to the controller 235. In this case, the medical image diagnostic apparatus 110 and the terminal device 140 create the stereoscopic image and the planar image and control the display thereof. Further, the creating of the stereoscopic image, the creating of the planar image, and the controlling of display may be implemented to be distributed in the devices included in the image processing system 1.

In the above-described embodiment, it has been described that the terminal device 140 displays the medical image obtained from the image archiving device 120. However, the embodiments are not limited thereto. For example, the terminal device 140 may be directly connected to the medical image diagnostic apparatus 110.

In the above-described embodiment, it has been described that the work station 130 obtains the volume data from the image archiving device 120. However, the embodiments are not limited thereto. For example, the work station 130 may obtain the volume data from the medical image diagnostic apparatus 110.

In the above-described embodiments, when the stereoscopic image is changed, the volume rendering processing is performed on the volume data in real time, but the embodiments are not limited thereto. For example, a plurality of disparity images in accordance with a plurality of viewing point locations may be created in advance and stored in advance. In this case, if the stereoscopic image creating unit accepts a command for changing the stereoscopic effect, the stereoscopic image creating unit creates a new stereoscopic image by appropriately selecting a disparity image group in accordance with a new disparity angle from the plurality of disparity images stored in advance.
(Both Designated Region and Background Region are Stereoscopic Images)

In the above-described embodiments, a method of displaying the stereoscopic image and the planar image in the designated region and the background region in the display surface, respectively is described. However, the embodiments are not limited thereto. For example, in the first to fourth embodiments, the stereoscopic images having different stereoscopic effects may be displayed in both the designated region and the background image. The difference in stereoscopic effects may be large enough to be noticeable such that it becomes the stereoscopic image and the planar image or very small so as to be indistinguishable. That is, the difference in stereoscopic effect may be arbitrarily changed. Further, the change of the stereoscopic effect or the enlargement/reduction ratio only for the stereoscopic image that is displayed in the designated region may be accepted. According to the above-described method, it is possible to change the stereoscopic effect or the enlargement/reduction ratio only for the region of interest.

In this case, for example, the work station 130 includes a first image creating unit, a second image creating unit, and a display controller. The first image creating unit creates a first image by performing the rendering processing on the volume data. The second image creating unit creates a second image having a different stereoscopic effect from the first image by performing the rendering processing on the volume data. The display controller controls to display the first image and the second image in the designated region and the background image, respectively. The display controller controls to three-dimensionally display the first image and the second image in the designated region and the background image, respectively. Further, the work station 130 accepts the change of the stereoscopic effect or the enlargement/reduction ratio for the stereoscopic image to be displayed in the designated region and the first image creating unit or the second image creating unit re-creates a new stereoscopic image in accordance with the accepted change.

(Stereoscopic Image on Separate Window)

In the above-described embodiments, a method of displaying the stereoscopic image and the planar image in the designated region and the background region in the display surface, respectively, is described. However, the embodiments are not limited thereto. For example, the planar image may be displayed in the entire region and the stereoscopic image may be displayed in a separate window.

In this case, for example, the work station 130 two-dimensionally displays the planar image on the stereoscopic display monitor and accepts the designation of a three-dimensionally displaying region as a stereoscopic image on the planar image. For example, the work station 130 accepts the designation of the region by the tool of the magnifier. The work station 130 three-dimensionally displays the stereoscopic image of the region accepting the designation in the separate window.

(Two Disparities or Six Disparities)

Figure 27A:
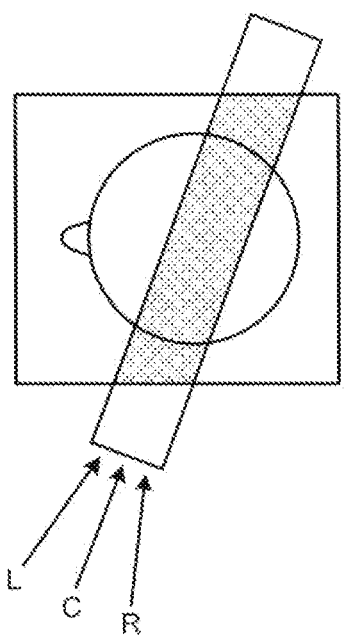
FIGS. 27A and 27B are views illustrating a stereoscopic image creating processing according to the other embodiment.
Figure 27B:
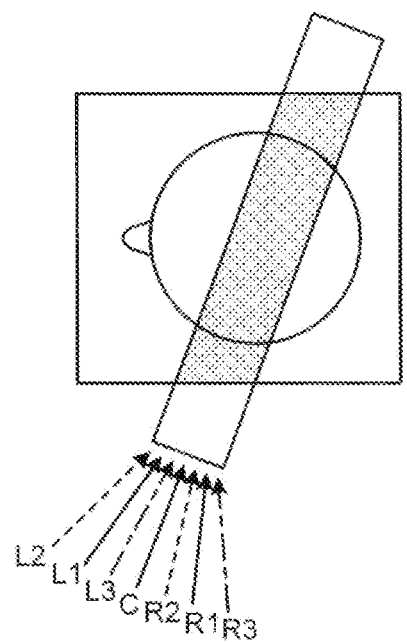

In the above-described embodiments, nine disparity images are described. However, the embodiments are not limited thereto, but, for example, an arbitrary disparity number such as two disparities or six disparities may be used. FIGS. 27A and 27B are views illustrating a stereoscopic image creating processing according to the other embodiments. In case of two disparities, as illustrated in FIG. 27A, the stereoscopic image is created using the designated viewing point location as "viewing point location C" and two points of "viewing point location L" and "viewing point location R" with "viewing point location C" in the middle of them as the rendering condition. In case of six disparities, as illustrated in FIG. 27B, the stereoscopic image is created using the designated viewing point location as "viewing point location C" and six points of "viewing point location L2", "viewing point location L1", "viewing point location L3, "viewing point location R2", "viewing point location R1", and "viewing point location R3 with "viewing point location C" in the middle of them as the rendering condition.

(The Others)

The components of the devices illustrated in the drawings are conceptual features and need not be physically configured as illustrated in the drawings. That is, the specific configuration of the distribution/integration of the devices is not limited to the drawings, but all or a part of the devices may be configured to be functionally or physically distributed or integrated in a predetermined unit in accordance with the various loads or usages. The processing functions performed in the devices may be entirely or partially implemented by a CPU and a program that is analyzed and executed in the CPU or implemented as hardware by a wired logic.

The image processing method described in the above embodiments may be implemented by executing the image processing program which is provided in advance by a computer such as a personal computer or a work station. The image processing program may be distributed through a network such as the Internet. Further, the program may be recorded in a computer readable recording medium such as a hard disk, a flexible disk (FD), a CD-ROM, an MO, and a DVD and executed by being read from the recording medium by a computer.

According to the image processing system and the method thereof of at least one of the above-described embodiments, it is possible to appropriately display a medical image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing system, comprising:
a first image creating unit configured to create a first image by performing a rendering processing on volume data which is three-dimensional medical image data;
a second image creating unit configured to create a second image different from the first image by performing the rendering processing on the volume data; and
a display controller configured to control to display the first image and the second image, respectively, in different ones of a designated region that is designated in a display surface of a display unit and a background region other than the designated region, wherein
the display unit displays a stereoscopic image by displaying a disparity image group having a predetermined disparity number, such that the stereoscopic image is viewable with a sense of depth or protrusion with respect to the display surface, and displays a planar image by replacing a plurality of identical images into the disparity image group to be displayed, such that the planar image is viewable without the sense of depth or protrusion,
the first image creating unit creates, as the first image, the disparity image group to be displayed as the stereoscopic image,
the second image creating unit creates the planar image, as the second image, in which an object is represented, the object being the same as or corresponding to an object represented in the stereoscopic image, and the display controller controls to display the stereoscopic image in any one of a designated region designated in a display surface of the display unit and a background region other than the designated region and display the planar image in the other region.

2. The image processing system of claim 1, wherein the planar image is a volume rendering image created from the volume data, a surface rendering image, an MPR (multi planer reconstruction) image, an MIP (maximum intensity projection) image, or an MinIP (minimum intensity projection) image.

3. The image processing system of claim 1, wherein the stereoscopic image is a stereoscopically viewable volume rendering image or an image in which a volume rendering image created from the volume data, a surface rendering image, an MPR image, an MIP image, or an MinIP image is attached on a surface of a stereoscopically viewable figure.

4. The image processing system of claim 1, further comprising:
a designation accepting unit configured to accept a designation of a stereoscopic region which is a designated region in which the stereoscopic image is displayed in a display surface of the display unit, wherein
the first image creating unit creates the disparity image group by performing the rendering processing on the volume data in accordance with the designated stereoscopic region,
the second image creating unit creates the planar image by performing the rendering processing on the volume data in accordance with the designated stereoscopic region, and
the display controller controls to superpose the stereoscopic image and the planar image and display the stereoscopic image and the planar image in the stereoscopic region and the background region, respectively.

5. The image processing system of claim 4, further comprising:
a cross-sectional position designation accepting unit configured to accept the designation of a cross-sectional position which is displayed as the cross-sectional image,
wherein the second image creating unit creates the cross-sectional image as the planar image in accordance with the designation of the cross-sectional position.

6. The image processing system of claim 4, wherein:
the designation accepting unit is further configured to accept a command of changing a stereoscopic region which is a designated region in which the stereoscopic image is displayed in a display surface of the display unit,
the first image creating unit is configured to create a disparity image group to be displayed as a new stereoscopic image by performing a rendering processing in accordance with the command,
the second image creating unit is configured to create a new planar image by performing a rendering processing in accordance with the command, and
the display controller is configured to control to superpose the new stereoscopic image and the new planar image and display the new stereoscopic image and the new planar image in the stereoscopic region and the background region, respectively.

7. The image processing system of claim 4, wherein:
the designation accepting unit is further configured to accept at least one of a command of changing a disparity angle of the stereoscopic image which is displayed in the display unit, and a command of changing an enlargement ratio or a reduction ratio of the stereoscopic image which is displayed in the display unit,
the first image creating unit is configured to create a disparity image group to be displayed as a new stereoscopic image by performing a rendering processing in accordance with the command, and
the display controller is configured to control to replace the stereoscopic image displayed in the display surface of the display unit with the new stereoscopic image.

8. The image processing system of claim 1, wherein:
the second image creating unit creates a cross-sectional image that displays a cross-section of an object that is represented in the stereoscopic image as the planar image, and
the display controller controls to display the cross-sectional image in any one of the designated region and the background region.

9. The image processing system of claim 1, further comprising:
an analyzing unit configured to analyze the medical image data and outputs the analysis result; and
a specifying unit configured to specify a predetermined region in the display surface of the display unit based on the analysis result,
wherein the display controller configured to control to superpose the stereoscopic image and the planar image and display the stereoscopic image in any one of a predetermined region specified based on the analysis result and a background region other than the predetermined region and the planar image in the other region, respectively.

10. The image processing system of claim 9, wherein:
the display controller displays a cross-sectional image that displays a cross-section of an object that is represented in the stereoscopic image as the planar image,
the specifying unit further specifies the cross-sectional position which is displayed as the cross-section image based on the analysis result, and
the second image creating unit creates the cross-sectional image as the planar image in accordance with the designation of the cross-sectional position specified based on the analysis result.

11. The image processing system of claim 9, wherein:
the display controller controls to display the stereoscopic image in a predetermined region specified based on the analysis result,
the specifying unit further specifies a disparity angle of the stereoscopic image based on the analysis result, and
the first image creating unit creates the stereoscopic image in accordance with the disparity angle specified based on the analysis result.

12. An image processing method that is executed by an image processing system, comprising:
creating, by a first image creating unit of the image processing system, a first image by performing a rendering processing on volume data which is three-dimensional medical image data;
creating, by a second image creating unit of the image processing system, a second image different from the first image by performing the rendering processing on the volume data; and
controlling, by a display controller of the image processing system, to display the first image and the second image, respectively, in different ones of a designated region that is designated in a display surface of a display unit and a background region other than the designated region, wherein the display unit displays the stereoscopic image by displaying a disparity image group having a predetermined disparity number, such that the stereoscopic image is viewable with a sense of depth or protrusion with respect to the display surface, and displays the planar image by replacing a plurality of identical images into the disparity image group to be displayed, such that the planar image is viewable without the sense of depth or protrusion, the first image creating unit creates, as the first image, the disparity image group to be displayed as the stereoscopic image, the second image creating unit creates the planar image, as the second image, in which an object is represented, the object being the same as or corresponding to an object represented in the stereoscopic image, and the display controller controls to display the stereoscopic image in any one of a designated region designated in a display surface of the display unit and a background region other than the designated region and display the planar image in the other region.

13. An image processing system, comprising:

a first image creating unit configured to create a first image of a stereoscopic image by performing a rendering processing on volume data which is three-dimensional medical image data;

a second image creating unit configured to create a second image of the stereoscopic image that is different from the first image by performing the rendering processing on the volume data; and a display controller configured to control to display the first image and the second image, respectively, in different ones of a designated region that is designated in a display surface of a display unit and a background region other than the designated region, wherein the display unit displays a stereoscopic image by displaying a disparity image group having a predetermined disparity number, such that the stereoscopic image is viewable with a sense of depth or protrusion with respect to the display surface, the first image creating unit creates, as the first image, a first disparity image group to be displayed as part of the stereoscopic image, and the second image creating unit creates a second disparity image group as the second image as part of the stereoscopic image that is different from the first image in a disparity angle, such that the second image has a different sense of depth or protrusion than the first image.

14. An image processing method that is executed by an image processing system, comprising:

creating, by a first image creating unit of the image processing system, a first image of a stereoscopic image by performing a rendering processing on volume data which is three-dimensional medical image data;

creating, by a second image creating unit of the image processing system, a second image of the stereoscopic image that is different from the first image by performing the rendering processing on the volume data; and controlling, by a display controller of the image processing system, to display the first image and the second image, respectively, in different ones of a designated region that is designated in a display surface of a display unit and a background region other than the designated region, wherein:

the display unit displays the stereoscopic image by displaying a disparity image group having a predetermined disparity number, such that the stereoscopic image is viewable with a sense of depth or protrusion with respect to the display surface, the first image creating unit creates, as the first image, a first disparity image group to be displayed as part of the stereoscopic image, and the second image creating unit creates a second disparity image group as the second image as part of the stereoscopic image that is different from the first image in a disparity angle, such that the second image has a different sense of depth or protrusion than the first image.

* * * * *